United States Patent
Opal et al.

(10) Patent No.: US 12,414,981 B2
(45) Date of Patent: Sep. 16, 2025

(54) JNK INHIBITORS FOR USE IN TREATING AND PREVENTING NEURODEGENERATIVE DISORDERS

(71) Applicant: Northwestern University, Evanston, IL (US)

(72) Inventors: Puneet Opal, Evanston, IL (US); Chandrakanth Reddy Edamakanti, Evanston, IL (US)

(73) Assignee: Northwestern University, Evanston, IL (US)

( * ) Notice: Subject to any disclaimer, the term of this patent is extended or adjusted under 35 U.S.C. 154(b) by 67 days.

(21) Appl. No.: 17/663,028

(22) Filed: May 12, 2022

(65) Prior Publication Data

US 2022/0362335 A1  Nov. 17, 2022

Related U.S. Application Data

(60) Provisional application No. 63/201,780, filed on May 12, 2021.

(51) Int. Cl.
 *A61K 38/00* (2006.01)
 *A61K 38/17* (2006.01)
 *A61P 25/28* (2006.01)

(52) U.S. Cl.
 CPC .......... *A61K 38/1709* (2013.01); *A61P 25/28* (2018.01)

(58) Field of Classification Search
 CPC ............................ A61K 38/1709; A61P 25/28
 See application file for complete search history.

(56) References Cited

U.S. PATENT DOCUMENTS

| | | | |
|---|---|---|---|
| 2010/0099691 A1* | 4/2010 | Boice | A61P 9/00 514/264.11 |
| 2020/0093883 A1* | 3/2020 | Combette | A61K 9/0063 |

OTHER PUBLICATIONS

Chia-Wei Lin, Chia-Hao Fan, Ya-Chin Chang, Hsiu Mei Hsieh-Li, ERK activation precedes Purkinje cell loss in mice with Spinocerebellar ataxia type 17, Neuroscience Letters, vol. 738, 2020.*
Albanito, L., Reddy, C. E. & Musti, A. M. c-Jun is essential for the induction of II-1β gene expression in in vitro activated Bergmann glial cells. Glia 59, 1879-1890, doi:10.1002/glia.21244 (2011).
Andoh, T. et al. Protective Effect of IL-18 on Kainate- and IL-1β-Induced Cerebellar Ataxia in Mice. The Journal of Immunology 180, 2322, doi:10.4049/jimmunol.180.4.2322 (2008).
Araujo, A. P. B., Carpi-Santos, R. & Gomes, F. C. A. The Role of Astrocytes in the Development of the Cerebellum. Cerebellum 18, 1017-1035, doi:10.1007/s12311-019-01046-0 (2019).
Ashizawa, T., Öz, G. & Paulson, H. L. Spinocerebellar ataxias: prospects and challenges for therapy development. Nat Rev Neurol 14, 590-605, doi:10.1038/s41582-018-0051-6 (2018).
Barnes, J. et al. Abnormalities in the Climbing Fiber-Purkinje Cell Circuitry Contribute to Neuronal Dysfunction in ATXN1[82Q] Mice. The Journal of neuroscience : the official journal of the Society for Neuroscience 31, 12778-12789, doi:10.1523/JNEUROSCI.2579-11.2011 (2011).
Bernaus, A., Blanco, S. & Sevilla, A. Glia Crosstalk in Neuroinflammatory Diseases. Frontiers in Cellular Neuroscience 14, doi:10.3389/fncel.2020.00209 (2020).
Binda, F., Pernaci, C. & Saxena, S. Cerebellar Development and Circuit Maturation: A Common Framework for Spinocerebellar Ataxias. Frontiers in neuroscience 14, 293-293, doi:10.3389/fnins.2020.00293 (2020).
Bogoyevitch, M. A. The isoform-specific functions of the c-Jun N-terminal Kinases (JNKs): differences revealed by gene targeting. Bioessays 28, 923-934, doi: 10.1002/bies.20458 (2006).
Buffo, A. & Rossi, F. Origin, lineage and function of cerebellar glia. Prog Neurobiol 109, 42-63, doi: 10.1016/j.pneurobio.2013.08.001 (2013).
Cerrato, V. Cerebellar Astrocytes: Much More Than Passive Bystanders In Ataxia Pathophysiology. J Clin Med 9, 757, doi:10.3390/jcm9030757 (2020).
Custer, S. K. et al. Bergmann glia expression of polyglutamine-expanded ataxin-7 produces neurodegeneration by impairing glutamate transport. Nat Neurosci 9, 1302-1311, doi:10.1038/nn1750 (2006).
Cvetanovic, M. Decreased expression of glutamate transporter GLAST in Bergmann glia is associated with the loss of Purkinje neurons in the spinocerebellar ataxia type 1. Cerebellum 14, 8-11, doi: 10.1007/s12311-014-0605-0 (2015).
Cvetanovic, M., Ingram, M., Orr, H. & Opal, P. Early activation of microglia and astrocytes in mouse models of spinocerebellar ataxia type 1. Neuroscience 289, 289-299, doi:10.1016/j.neuroscience.2015.01.003 (2015).
Cvetanovic, M., Patel, J. M., Marti, H. H., Kini, A. R. & Opal, P. Vascular endothelial growth factor ameliorates the ataxic phenotype in a mouse model of spinocerebellar ataxia type 1. Nat Med 17, 1445-1447, doi:10.1038/nm.2494 (2011).
De Zeeuw, C. I. & Hoogland, T. M. Reappraisal of Bergmann glial cells as modulators of cerebellar circuit function. Front Cell Neurosci 9, 246, doi:10.3389/fncel.2015.00246 (2015).
Diallo, A. et al. Survival in patients with spinocerebellar ataxia types 1, 2, 3, and 6 (EUROSCA): a longitudinal cohort study. The Lancet. Neurology 17, 327-334, doi:10.1016/s1474-4422(18)30042-5 (2018).
Dooves, S. et al. Bergmann glia translocation: a new disease marker for vanishing white matter identifies therapeutic effects of Guanabenz treatment. Neuropathology and applied neurobiology 44, 391-403, doi:10.1111/nan.12411 (2018).
Dürr, A. et al. Spinocerebellar ataxia 3 and Machado-Joseph disease: clinical, molecular, and neuropathological features. Annals of neurology 39, 490-499, doi:10.1002/ana.410390411 (1996).
Ebner, B. A. et al. Purkinje Cell Ataxin-1 Modulates Climbing Fiber Synaptic Input in Developing and Adult Mouse Cerebellum. The Journal of Neuroscience 33, 5806-5820, doi:10.1523/jneurosci.6311-11.2013 (2013).

(Continued)

*Primary Examiner* — Jeanette M Lieb
(74) *Attorney, Agent, or Firm* — Quarles & Brady LLP

(57) ABSTRACT

Disclosed are compounds, compositions, and methods for treating and/or preventing neurodegenerative diseases and disorders. Particularly disclosed are compounds, compositions, and methods for treating and/or preventing neurodegenerative diseases and disorders such as spinocerebellar ataxia type 1 (SCA1) by administering a JNK inhibitor.

7 Claims, 15 Drawing Sheets
(11 of 15 Drawing Sheet(s) Filed in Color)

(56) References Cited

OTHER PUBLICATIONS

Edamakanti, C. R., Do, J., Didonna, A., Martina, M. & Opal, P. Mutant ataxin1 disrupts cerebellar development in spinocerebellar ataxia type 1. J Clin Invest 128, 2252-2265, doi:10.1172/jci96765 (2018).

Evert, B. O. et al. Inflammatory genes are upregulated in expanded ataxin-3-expressing cell lines and spinocerebellar ataxia type 3 brains. J Neurosci 21, 5389-5396, doi:10.1523/jneurosci.21-15-05389.2001 (2001).

Ferro, A., Sheeler, C., Rosa, J. G. & Cvetanovic, M. Role of Microglia in Ataxias. Journal of molecular biology 431, 1792-1804, doi:10.1016/j.jmb.2019.01.016 (2019).

Gleichman, A. J. & Carmichael, S. T. Glia in neurodegeneration: Drivers of disease or along for the ride? Neurobiology of Disease 142, 104957, doi:https://doi.org/10.1016/j.nbd.2020.104957 (2020).

Grondin, B. et al. c-Jun homodimers can function as a context-specific coactivator. Mol Cell Biol 27, 2919-2933, doi:10.1128/mcb.00936-06 (2007).

Hayashi, C., Suzuki, N., Takahashi, R. & Akazawa, C. Development of type I/II oligodendrocytes regulated by teneurin-4 in the murine spinal cord. Scientific Reports 10, 8611, doi:10.1038/s41598-020-65485-0 (2020).

Hepp Rehfeldt, S. C., Majolo, F., Goettert, M. I. & Laufer, S. c-Jun N-Terminal Kinase Inhibitors as Potential Leads for New Therapeutics for Alzheimer's Diseases. Int J Mol Sci 21, doi:10.3390/ijms21249677 (2020).

Hewett, S. J., Jackman, N. A. & Claycomb, R. J. Interleukin-1β in Central Nervous System Injury and Repair. Eur J Neurodegener Dis 1, 195-211 (2012).

Holzberg D, et al. Disruption of the c-JUN-JNK complex by a cell-permeable peptide containing the c-JUN delta domain induces apoptosis and affects a distinct set of interleukin-1-induced inflammatory genes. J Biol Chem. 2003;278(41):40213-23.

Hong, J. et al. Lipopolysaccharide administration for a mouse model of cerebellar ataxia with neuroinflammation. Sci Rep 10, 13337, doi: 10.1038/s41598-020-70390-7 (2020).

Hu, Y. S. et al. Self-assembling vascular endothelial growth factor nanoparticles improve function in spinocerebellar ataxia type 1. Brain, doi:10.1093/brain/awy328 (2019).

Iltis, I. et al. (1)H MR spectroscopy in Friedreich's ataxia and ataxia with oculomotor apraxia type 2. Brain Res 1358, 200-210, doi:10.1016/j.brainres.2010.08.030 (2010).

Jang, S., Kelley, K. W. & Johnson, R. W. Luteolin reduces IL-6 production in microglia by inhibiting JNK phosphorylation and activation of AP-1. Proc Natl Acad Sci U S A 105, 7534-7539, doi: 10.1073/pnas.0802865105 (2008).

Jin, J. J., Kim, H. D., Maxwell, J. A., Li, L. & Fukuchi, K. Toll-like receptor 4-dependent upregulation of cytokines in a transgenic mouse model of Alzheimer's disease. J Neuroinflammation 5, 23, doi:10.1186/1742-2094-5-23 (2008).

Joers, J. M. et al. Neurochemical abnormalities in premanifest and early spinocerebellar ataxias. Annals of neurology 83, 816-829, doi:10.1002/ana.25212 (2018).

Kim, B. J. et al. In vitro and in vivo neuroprotective effects of cJun N-terminal kinase inhibitors on retinal ganglion cells. Mol Neurodegener 11, 30, doi:10.1186/s13024-016-0093-4 (2016).

Kim, J. H., Lukowicz, A., Qu, W., Johnson, A. & Cvetanovic, M. Astroglia contribute to the pathogenesis of spinocerebellar ataxia Type 1 (SCA1) in a biphasic, stage-of-disease specific manner. Glia 66, 1972-1987, doi:10.1002/glia.23451 (2018).

Klockgether, T., Mariotti, C. & Paulson, H. L. Spinocerebellar ataxia. Nat Rev Dis Primers 5, 24, doi:10.1038/s41572-019-0074-3 (2019).

Leung, A. W. & Li, J. Y. H. The Molecular Pathway Regulating Bergmann Glia and Folia Generation in the Cerebellum. Cerebellum 17, 42-48, doi:10.1007/s12311-017-0904-3 (2018).

Liddelow, S. A. et al. Neurotoxic reactive astrocytes are induced by activated microglia. Nature 541, 481-487, doi:10.1038/nature21029 (2017).

Miyake, K. Innate recognition of lipopolysaccharide by Toll-like receptor 4-MD-2. Trends Microbiol 12, 186-192, doi:10.1016/j.tim.2004.02.009 (2004).

Ngkelo, A., Meja, K., Yeadon, M., Adcock, I. & Kirkham, P. A. LPS induced inflammatory responses in human peripheral blood mononuclear cells is mediated through NOX4 and Giα dependent PI-3kinase signalling. J Inflamm (Lond) 9, 1, doi:10.1186/1476-9255-9-1 (2012).

Oppenheimer, D. R. Brain lesions in Friedreich's ataxia. Can J Neurol Sci 6, 173-176, doi:10.1017/s0317167100119596 (1979).

Park, J. Y., Joo, K. & Woo, S. J. Ophthalmic Manifestations and Genetics of the Polyglutamine Autosomal Dominant Spinocerebellar Ataxias: A Review. Front Neurosci 14, 892, doi:10.3389/fnins.2020.00892 (2020).

Perez-Catalan, N. A., Doe, C. Q. & Ackerman, S. D. The role of astrocyte-mediated plasticity in neural circuit development and function. Neural Dev 16, 1, doi:10.1186/s13064-020-00151-9 (2021).

Qu, W. et al. Inhibition of colony-stimulating factor 1 receptor early in disease ameliorates motor deficits in SCA1 mice. J Neuroinflammation 14, 107, doi:10.1186/s12974-017-0880-z (2017).

Reddy, C. E. et al. Multisite phosphorylation of c-Jun at threonine 91/93/95 triggers the onset of c-Jun pro-apoptotic activity in cerebellar granule neurons. Cell Death Dis 4, e852, doi:10.1038/cddis.2013.381 (2013).

Robinson, K. J., Watchon, M. & Laird, A. S. Aberrant Cerebellar Circuitry in the Spinocerebellar Ataxias. Front Neurosci 14, 707, doi:10.3389/fnins.2020.00707 (2020).

Rüb, U. et al. Clinical features, neurogenetics and neuropathology of the polyglutamine spinocerebellar ataxias type 1, 2, 3, 6 and 7. Prog Neurobiol 104, 38-66, doi:10.1016/j.pneurobio.2013.01.001 (2013).

Ruegsegger, C. et al. Impaired mTORC1-Dependent Expression of Homer-3 Influences SCA1 Pathophysiology. Neuron 89, 129-146, doi:10.1016/j.neuron.2015.11.033 (2016).

Sasaki, T. et al. Application of an optogenetic byway for perturbing neuronal activity via glial photostimulation. Proc Natl Acad Sci U S A 109, 20720-20725, doi:10.1073/pnas.1213458109 (2012).

Schuster, K. H. et al. Impaired Oligodendrocyte Maturation Is an Early Feature in SCA3 Disease Pathogenesis. J Neurosci 42, 1604-1617, doi:10.1523/jneurosci.1954-20.2021 (2022).

Sheeler, C. et al. Glia in Neurodegeneration: The Housekeeper, the Defender and the Perpetrator. Int J Mol Sci 21, doi:10.3390/ijms21239188 (2020).

Shiwaku, H., Yagishita, S., Eishi, Y. & Okazawa, H. Bergmann glia are reduced in spinocerebellar ataxia type 1. NeuroReport 24, 620-625 610.1097/WNR.1090b1013e32836347b32836347.

Shuvaev, A. N. et al. Chronic optogenetic stimulation of Bergman glia leads to dysfunction of EAAT1 and Purkinje cell death, mimicking the events caused by expression of pathogenic ataxin-1. Neurobiology of Disease 154, 105340, doi: https://doi.org/10.1016/j.nbd.2021.105340 (2021).

Sochocka, M., Diniz, B. S. & Leszek, J. Inflammatory Response in the CNS: Friend or Foe? Molecular Neurobiology 54, 8071-8089, doi:10.1007/s12035-016-0297-1 (2017).

Stevenson, R., Samokhina, E., Rossetti, I., Morley, J. W. & Buskila, Y. Neuromodulation of Glial Function During Neurodegeneration. Frontiers in Cellular Neuroscience 14, doi:10.3389/fncel.2020.00278 (2020).

Sullivan, R., Yau, W. Y., O'Connor, E. & Houlden, H. Spinocerebellar ataxia: an update. Journal of Neurology 266, 533-544, doi:10.1007/s00415-018-9076-4 (2019).

Tan, Y.-L., Yuan, Y. & Tian, L. Microglial regional heterogeneity and its role in the brain. Molecular Psychiatry 25, 351-367, doi:10.1038/s41380-019-0609-8 (2020).

Tejwani, L. & Lim, J. Pathogenic mechanisms underlying spinocerebellar ataxia type 1. Cell Mol Life Sci 77, 4015-4029, doi:10.1007/s00018-020-03520-z (2020).

Tejwani, L. et al. Longitudinal single-cell transcriptional dynamics throughout neurodegeneration in SCA1. bioRxiv, 2021.2010.2022.465444, doi:10.1101/2021.10.22.465444 (2021).

(56) References Cited

OTHER PUBLICATIONS

Vaishnav, D., Jambal, P., Reusch, J. E. & Pugazhenthi, S. SP600125, an inhibitor of c-jun N-terminal kinase, activates CREB by a p38 MAPK-mediated pathway. Biochem Biophys Res Commun 307, 855-860, doi:10.1016/s0006-291x(03) 01287-7 (2003).

Waetzig, V. et al. c-Jun N-terminal kinases (JNKs) mediate pro-inflammatory actions of microglia. Glia 50, 235-246, doi:10.1002/glia.20173 (2005).

Wang, W. et al. SP600125, a new JNK inhibitor, protects dopaminergic neurons in the MPTP model of Parkinson's disease. Neurosci Res 48, 195-202, doi:10.1016/j.neures.2003.10.012 (2004).

Watase, K. et al. A Long CAG Repeat in the Mouse Sca1 Locus Replicates SCA1 Features and Reveals the Impact of Protein Solubility on Selective Neurodegeneration. Neuron 34, 905-919, doi:http://dx.doi.org/10.1016/S0896-6273(02)00733-X (2002).

Zahr, N. M., Mayer, D., Rohlfing, T., Sullivan, E. V. & Pfefferbaum, A. Imaging neuroinflammation? A perspective from MR spectroscopy. Brain Pathol 24, 654-664, doi:10.1111/bpa.12197 (2014).

Zhao, J. et al. Neuroinflammation induced by lipopolysaccharide causes cognitive impairment in mice. Sci Rep 9, 5790, doi:10.1038/s41598-019-42286-8 (2019).

Orr, H. T. SCA1-Phosphorylation, a regulator of Ataxin-1 function and pathogenesis. Prog Neurobiol. 2012, 99, 179-185.

Taniguchi, J. B. et al. RpA1 ameliorates symptoms of mutant ataxin-1 knock-in mice and enhances DNA damage repair. Hum Mol Genet. 2016, 25, 4432-4447.

Venkatraman, A. et al. The histone deacetylase HDAC3 is essential for Purkinje cell function, potentially complicating the use of HDAC inhibitors in SCA1. Hum Mol Genet. 2014, 23, 3733-3745.

Lee, A. et al. Isolation of neural stem cells from the postnatal cerebellum. Nat Neurosci. 2005, 8, 723-729.

Fleming, J. T. et al. The Purkinje Neuron Acts as a Central Regulator of Spatially and Functionally Distinct Cerebellar Precursors. Dev. Cell 2013, 27, 278-292.

Li, P. et al. A population of Nestin expressing progenitors in the cerebellum exhibits increased tumorigenicity. Nat Neurosci. 2013, 16, 1737-1744.

Blot, A. et al. Ultra-rapid axon-axon ephaptic inhibition of cerebellar Purkinje cells by the pinceau. Nat Neurosci. 2014, 17, 289-295.

Kim, et al. Optogenetic Mapping of Cerebellar Inhibitory Circuitry Reveals Spatially Biased Coordination of Interneurons via Electrical Synapses. Cell Rep. 2014, 7, 1601-1613.

Rieubland, S. et al. Structured Connectivity in Cerebellar Inhibitory Networks. Neuron. 2014, 81, 913-929.

Iwakura, A. et al. Lack of Molecular-Anatomical Evidence for GABAergic Influence on Axon Initial Segment of Cerebellar Purkinje Cells by the Pinceau Formation. J. Neurosci. 2012, 32, 9448-9439.

Sudarov, A. et al. Ascl1 Genetics Reveals Insights into Cerebellum Local Circuit Assembly. J. Neurosci. 2011, 31, 11055-11069.

\* cited by examiner

JNK INHIBITORS FOR USE IN TREATING AND PREVENTING NEURODEGENERATIVE DISORDERS

CROSS-REFERENCE TO RELATED APPLICATIONS

The present application claims priority to U.S. Provisional Patent Application No. 63/201,780, filed May 12, 2021, the entire contents of which are hereby incorporated by reference.

STATEMENT REGARDING FEDERALLY SPONSORED RESEARCH

This invention was made with government support under NS082351 awarded by National Institutes of Health. The government has certain rights in the invention.

FIELD OF THE INVENTION

The disclosed technology is generally directed to compounds, compositions and methods for treating and/or preventing neurodegenerative diseases and disorders. More particularly the technology is directed to compounds, compositions and methods for treating and/or preventing neurodegenerative diseases and disorders such as spinocerebellar ataxias by administering a JNK inhibitor.

BACKGROUND OF THE INVENTION

The spinocerebellar ataxias (SCAs) are a group of autosomal dominant disorders characterized by adult onset cerebellar and brainstem degeneration. They are progressive and untreatable, and patients eventually die from respiratory complications such as aspiration and subsequent pneumonia[1-3]. The more prevalent SCAs are caused by CAG trinucleotide genomic expansions. These mutations occur in the coding region of the relevant gene and therefore result in an expanded polyglutamine tract in the encoded proteins. The polyglutamine ataxias include SCAs 1, 2, 3, 6, 7, and 17 and a related ataxic syndrome Dentatorubral-pallidoluysian atrophy[3-4]. Together they account for approximately 80% of the currently genetically elucidated SCAs[5]. The rest are caused by either microsatellite repeats or conventional mutations such as deletions or point mutations that alter the coding region of the affected genes[6].

It is not entirely clear why the SCAs display regional vulnerability of the cerebellum, as reflected in early and progressive ataxia. The mutant proteins themselves are expressed in a largely ubiquitous manner. In the past, most of the focus has been on understanding cell autonomous changes in vulnerable neurons, most notably Purkinje neurons because of visible dystrophic changes and their importance to cerebellar function. But other neuronal populations, particularly those of the cerebellum and brainstem, also contribute to the syndrome.

Endothelial cells contribute to the microvasculature, while glial cells contribute to the normal functioning of neurons. These non-neuronal cells participate in inflammation as evidenced by numerous pathological and magnetic resonance spectroscopy-based imaging studies in human patients[16-18]. As with neurons, glial cells also display alterations in gene expression which show longitudinal changes as the disease progresses[19,20]. Indeed, gene expression changes are observed in all major glial populations: oligodendrocytes that ensheath neurons, astrocytes which participate in complex neuronal-glial interactions to support neurons, and microglia, the resident macrophages that protect neurons from stress and activating inflammatory responses[21-23]. Despite these findings the role of glial cells in pathogenesis of spinocerebellar ataxias has been difficult to decipher, hampering development of treatments for neurodegenerative disorders, such as SCAs

BRIEF SUMMARY OF THE INVENTION

Disclosed herein are methods and compositions for treating a subject comprising the administration of an effective amount of a c-Jun N-terminal kinase (JNK) inhibitor to a subject in need of a treatment for a neurodegenerative disease or disorder, including spinocerebellar ataxias to decrease phosphorylation of c-Jun and decrease inflammation in Bergmann glia.

One aspect of the technology provides for a method for treating and/or preventing a neurodegenerative disease or disorder in a subject in need thereof, the method comprising administering to the subject an effective amount of a JNK inhibitor. In some embodiments, the neurodegenerative disease is spinocerebellar ataxia. In particular embodiments, the neurodegenerative disease is spinocerebellar ataxia type 1.

In some embodiments, the subject in need thereof has Bergmann glia (BG)-specific JNK dependent c-Jun phosphorylation.

In some embodiments, the JNK inhibitor is a blood-brain barrier permeating compound. In some embodiments, JNK inhibitor inhibits one or more isoforms of JNK. In a particular embodiment the JNK inhibitor is SP600125.

In some embodiments the method further comprises testing for the presence of a biomarker for the neurodegenerative disease or disorder in a biological sample from the subject and administering the effective amount of the JNK inhibitor if the biological sample tests positive for the biomarker.

Another aspect provides for a pharmaceutical composition comprising the effective amount of the JNK inhibitor for treating and/or preventing a neurodegenerative disease or disorder in the subject in need thereof and a pharmaceutically acceptable excipient, carrier, or diluent.

Another aspect of the invention provides for a method for treating and/or preventing neuroinflammation in a subject in need thereof, the method comprising administering to the subject an effective amount of a INK inhibitor.

In some embodiments, the subject has Bergmann glia (BG) inflammation. In further embodiments, the BG release a proinflammatory cytokine. In a particular embodiment, the BG release IL-1β.

In some embodiments, the method further comprises testing for the presence of a biomarker for the neuroinflammation in a biological sample from the subject and administering the effective amount of the JNK inhibitor if the biological sample tests positive for the biomarker.

Another aspect of the technology provides for a pharmaceutical composition comprising the effective amount of the INK inhibitor for treating and/or preventing neuroinflammation in the subject in need thereof and a pharmaceutically acceptable excipient, carrier, or diluent.

Another aspect of the technology provides for a method for treating and/or preventing motor impairment in a subject in need thereof, the method comprising administering to the subject an effective amount of a JNK inhibitor. In some embodiments, the subject is in need of treatment and/or prevention of a spinocerebellar ataxia. In some embodiments, the subject is in need of treatment and/or prevention of Bergmann glia (BG) inflammation. In some embodiments, the method further comprises testing for the presence of a biomarker for motor impairment in a biological sample from the subject and administering the effective amount of the INK inhibitor if the biological sample tests positive for the biomarker.

Another aspect of the technology provides for a pharmaceutical composition comprising an effective amount of the INK inhibitor for treating and/or preventing motor impairment in the subject in need thereof and a pharmaceutically acceptable excipient, carrier, or diluent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
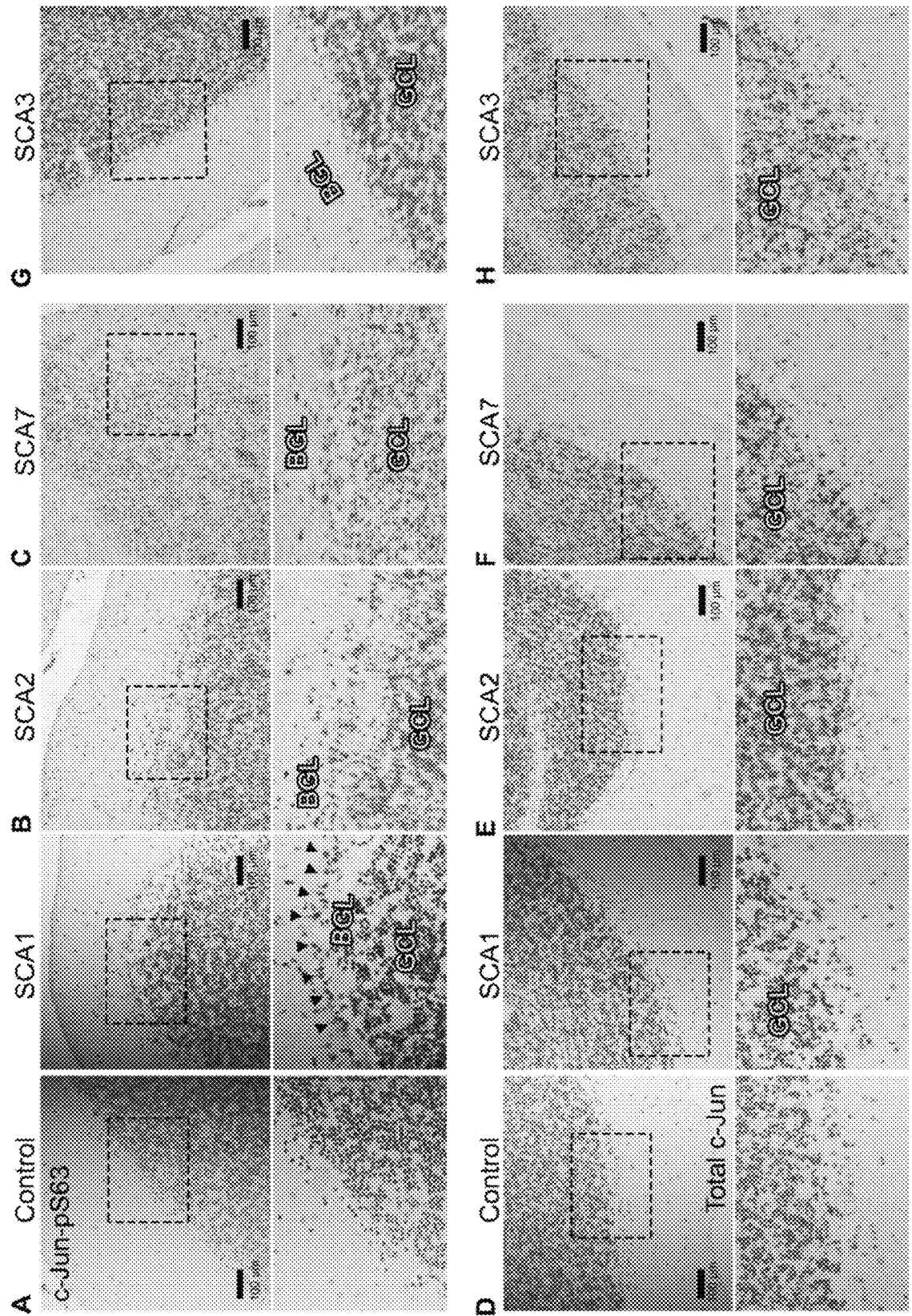
FIG. 1. Spinocerebellar ataxia patients exhibit Bergmann glia-specific c-Jun phosphorylation. (A-D) HRP-DAB immunostaining of human cerebellum from patients with (A) SCA1, (B) SCA2, (C) SCA7, and (G) SCA3 using c-Jun phosphorylation (c-Jun-pS63) antibody. Black-boxed regions represent the corresponding higher-magnification images shown below each photo. (E-H) HRP-DAB immunostaining of human cerebellum from patients with (D) SCA1, (E) SCA2, (F) SCA7, and (H) SCA3 using total c-Jun antibody. Black-boxed regions represent the corresponding higher-magnification images shown below each photo. In all panels nuclei are counterstained with hematoxylin. Scale bar=100 µm. Representative images are shown. BGL: Bergmann Glia Layer; GCL: Granular Cell Layer. We performed staining on multiple SCA1 (n=4), SCA2 (n=3), SCA3 (n=3), and SCA7 (n=3) samples, as well as age-matched controls (n=4).

Described here are compositions and methods for treating neurodegenerative diseases, including spinocerebellar ataxias, with a cJun N-terminal kinase (JNK) inhibitor. As demonstrated in the Examples, inhibitors of JNK are effective for reducing inflammation in Bergman glia cells, improving ataxias, and improving motor coordination.

Methods for treating subjects with the compounds disclosed herein are provided. Suitably, the methods for treating a subject comprise administering to the subject an effective amount of one or more inhibitors of JNK or a pharmaceutical composition comprising the effective amount of one or more inhibitors of JNK. As used herein, a "subject" maybe be interchangeable with "patient" or "individual" and means an animal, which may be a human or non-human animal, in need of treatment. In particular embodiments, the subject is a human subject.

As used herein, the terms "treating" or "to treat" each mean to alleviate symptoms, eliminate the causation of resultant symptoms either on a temporary or permanent basis and/or to prevent or slow the appearance or to reverse the progression or severity of resultant symptoms of the named disease or disorder. As such, the methods disclosed herein encompass both therapeutic and prophylactic administration. In some embodiments, the subject is responsive to therapy with one or more of the compounds disclosed herein in combination with one or more additional therapeutic agents.

As used herein the term "effective amount" refers to the amount or dose of the compound that provides the desired effect. In some embodiments, the effective amount is the amount or dose of the compound, upon single or multiple dose administration to the subject, which provides the desired effect in the subject under diagnosis or treatment. JNK inhibitors may be administered to a subject in an effective amount in such that the one or more isoforms of JNK is inhibited. Suitably, the desired effect may be slowing neurodegeneration, halting neurodegeneration, reversing neurodegeneration, reducing neuroinflammation, improving motor coordination, or combinations thereof. In some embodiments, the effective amount of the JNK results in slowing neurodegeration, reducing neuroinflammation, and improving motor coordination.

An effective amount can be readily determined by those of skill in the art, including an attending diagnostician, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A "subject in need of treatment" may include a subject having a disease, disorder, or condition that may be characterized by a neurodegenerative disease or disorder or neuroinflammation associated with or that contributes to the development or progression of a neurodegenerative disease or disorder.

A neurodegenerative disease or disorder is caused by the progressive loss of structure or function of neurons. Other, nonlimiting cell types that may also contribute to a neurodegenerative disease or disorder include, glial cells such as astrocytes and Bergmann glia.

A neurodegenerative disease or disorder may result in motor impairment. Motor impairment is the partial or total loss of function of a body part, usually a limb or limbs caused by trauma, disease or any other condition the muscular-skeletal system, spinal cord, or sensory motor nerves. This may result in altered muscle tone, unsteady gait, muscle weakness, poor stamina, lack of muscle control, or total paralysis.

Spinocerebellar ataxias (SCA) is a neurodegenerative disease or disorder that is progressive and degenerative changes in the part of the brain related to movement control, such as the cerebellum and sometimes in the spinal cord. SCAs are known to be caused by CAG trinucleotide genomic expansions. These mutations occur in the coding region of the relevant gene and therefore result in an expanded polyglutamine tract in the encoded protein. These polyglutamate disorders include SCAs 1, 2, 3, 6, 7, and 17 as well as related ataxic syndromes including Dentatorubral-pallidoluysian atrophy, Huntington disease, and spino-bulbar muscular atrophy.

Although the Examples have focused on the use of JNK inhibitors to treat or prevent SCA1 (i.e., an SCA caused by an expanded number of trinucleotide repeats in the polyglutamine tract of the ATXN1 gene), JNK inhibitors may also be used to treat or prevent other SCA (e.g., other polyglutamine ataxias, such as SCAs 2, 3, 6, 7, and 17, and also those caused by other mutations), familial ataxia (e.g., autosomal recessive and mitochondrial) and other sporadic or acquired ataxias that are also characterized by neuroinflammation.

Spinocerebellar ataxias pathology occurs within neuronal, endothelial, and glial cells—including astrocytes microglia and oligodendrocytes—of the central nervous system. Specifically, these include Purkinje neurons, olivary neurons, molecular layer interneurons as well as cranial nerve nuclei including the vagus and hypoglossal. Non-neuronal cells include astrocytes—including fibrous astrocytes, protoplasmic or velate astrocytes and Bergmann glia (BG). Bergmann glia cells may be called Golgi epithelial cells, radial epithelial cells or radial astrocytes. Bergmann glia are unipolar astrocytes derived from radial glia. BG are regionally specialized radial astrocytes that closely align with Purkinje cells in the cerebellum. BG also express abundant levels of c-Jun, a prototypical member of the Jun family of nuclear factors that is activated by phosphorylation and heterodimerizes with Fos (or ATF and CREB family members) to trigger an inflammatory cascade[28].

Neuroinflammation is inflammation of the nervous tissue. Neuroinflammation is mediated by the production of cytokines, chemokines, reactive oxygen species, and secondary messengers. Neuroinflammation can be activated by the central nervous system's innate immune system including glial cells, or by peripheral immune cells which pass the blood brain barrier. Neuroinflammation may be evaluated by levels of cytokine or other small molecules.

The Examples demonstrate that Bergmann glia (BG) are unique among the glial population of the cerebellum in that they express abundant levels of c-Jun, a prototypical member of the Jun family of nuclear factors that is activated by phosphorylation and heterodimerizes with Fos (or ATF and CREB family members) to trigger an inflammatory cascade. This uniqueness allows pharmacological intervention to tamp down BG-specific inflammation.

c-Jun is a protein that in humans is encoded by the JUN gene. c-Jun N-terminal kinases (JNKs) are kinases that bind and phosphorylate c-Jun on Ser-63 and Ser-73 within its transcriptional activation domain. They belong to the mitogen-activated protein kinase family, and are responsive to stress stimuli, such as cytokines, ultraviolet irradiation, heat shock, and osmotic shock. The JNKs consist of ten isoforms derived from alternative mRNA splicing of three genes: JNK1 (four isoforms), JNK2 (four isoforms) and JNK3 (two isoforms). As used herein, isoforms are a set of highly similar proteins that originate from a single gene or gene family and are the result of genetic differences. JNK isoforms may have distinct localization and function. "JNK" means a protein or an isoform thereof expressed by a JNK 1, JNK 2, or JNK 3 gene.

As used herein, JNK inhibitors are kinase inhibitors that can block or prevent the action or function or phosphorylation of JNKs. A person skilled in the art will understand that the term "inhibitor", as used herein, does not comprise compounds which irreversibly destroy the c-Jun N-terminal kinase (JNK) molecule and/or kinase activity. Furthermore, the term "inhibiting JNK activity" as used herein, refers to the inhibition of the kinase activity of c-Jun N-terminal kinase (JNK). Furthermore, a "JNK inhibitor" of the present invention inhibits JNK activity, e.g. exhibits with regard to the inhibition of human JNK mediated phosphorylation of a c-Jun substrate. The JNK inhibitor can be an anthrapyrazolone. Such inhibitors include SP600125. SP600125 (anthra [1,9]pyrazol-6 (2H)-one or 1,9-pyrazoloanthrone; CAS No.: 129-56-6) is a reversible ATP-competitive inhibitor and a strong inhibitor of c-Jun N-terminal kinase catalytic activity. SP600125 inhibits JNK1, JNK2 and JNK3 with a high specificity and inhibits the activation and phosphorylation of c-Jun as well as expression of inflammatory genes. Other inhibitors of JNK may include but are not limited to INK-IN-1 (CAS No.: 2745108-35-2), INK-IN-8 (CAS No.: 1410880-22-6), SR-3306 (N-[4-[3-(6-methylpyridin-3-yl)-1,2,4-triazol-1-yl]phenyl]-4-(3-morpholin-4-ylphenyl)pyrimidin-2-amine), TAT-JNK-III (Holzberg D, et al. Disruption of the c-JUN-INK complex by a cell-permeable peptide containing the c-JUN delta domain induces apoptosis and affects a distinct set of interleukin-1-induced inflammatory genes. J Biol Chem. 2003; 278(41):40213-23), AS601245 (CAS No.: 345987-15-7), AS602801 (CAS No.: 848344-36-5), AEG 3482 (CAS No.: 63735-71-7), D-JNKi (CAS No.: 1198367-70-2), Tanzisertib (CAS No.: 899805-25-5), XG-102 (D-JNK-1) (CAS No.: 1445179-97-4), and CC-401 (CAS No.: 395104-30-0). Inhibitors of JNK may be used singularly or in combination with two, three, four or more other combination of JNK inhibitors.

JNK inhibitors, such as SP600125, may be cell permeable and cross the blood brain barrier. Cell permeable molecules, including inhibitors, are able to pass through the membrane of a cell. The blood-brain barrier (BBB) is a highly selective semipermeable border of endothelial cells that prevents solutes in the circulating blood from non-selectively crossing into the extracellular fluid of the central nervous system where neurons reside. Compounds that are capable of permeating the BBB tend to have low molecular weight (e.g., less than 400 Da) and high lipid solubility. In some embodiments, the administered JNK inhibitors may be cell permeable and able to pass from circulation through the BBB in an effective amount to alter c-Jun function.

In some embodiments, the administered INK inhibitors may be incapable of permeating the BBB or have low permeability across the BBB. When such INK inhibitors are to be used in the disclosed methods, those of ordinary skill in the art can employ strategies for delivery of the INK inhibitor to the brain.

In some embodiments, the INK inhibitor may be co-administered with substance or compound to enhance permeability. In some embodiments, the JNK inhibitors is administered with a brain-delivery carrier or vehicle for delivery. Exemplary brain-delivery carriers and vehicles, include without limitation, viral vectors, nanoparticles, exosomes, and the like. In some embodiments, the JNK inhibitor may be co-administered with a brain permeability enhancer to transiently open the BBB.

In some embodiments, the INK inhibitor may be administered by a route that avoids the BBB. For example, the INK inhibitor may be administered nasally or by direct injection into the brain.

The INK inhibitors disclosed herein may be formulated as pharmaceutical compositions that include: an effective amount of one or more INK inhibitors and one or more pharmaceutically acceptable carriers, excipients, or diluents. Where a substance or compound is used the enhance permeability of the INK inhibitor, the substance or compound may be included in the pharmaceutical composition comprising the JNK inhibitor or provided in a separate pharmaceutical composition.

The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures. The compounds for use according to the methods disclosed herein may be administered as a single compound or a combination of compounds.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Pharmaceutically acceptable esters and amides of the compounds can also be employed in the compositions and methods disclosed herein.

In addition, the methods disclosed herein may be practiced using solvate forms of the compounds or salts, esters, and/or amides, thereof. Solvate forms may include ethanol solvates, hydrates, and the like.

In the present disclosure, a biomarker may be used to identify subjects that can benefit from the treatments disclosed herein. As used herein, biomarker is a measurable indicator of some biological state or condition. A biomarker is a characteristic that is objectively measured and evaluated as an indicator of normal biological processes, pathogenic processes, or pharmacologic responses to a therapeutic intervention. The biomarker may be a molecular biomarker, a cellular biomarker, a digital biomarker, a behavioral biomarker, or an imaging biomarker. The biomarker may be evaluated from a biological sample such as blood, soft tissue, tissue biopsy or sample or urine. As used herein, a biomarker may be an indicator of inflammation or a cell type specific marker.

Indicators of inflammation include, cytokines and other proteins or small molecules that indicate a state of inflammation. Inflammation involves activation of the immune system in response to harmful stimuli, such as pathogens, infections, stimulants, or cellular damage. As a stylized response, inflammation is one mechanism of innate immunity, which is compared to acquired immunity that is specific for each pathogen. Inflammation can be classified as either acute or chronic. Generally speaking, acute inflammation is mediated by granulocytes, and chronic inflammation is mediated by mononuclear cells such as monocytes and lymphocytes. Inflammation includes inflammatory cytokines.

Cytokines are a broad category of small proteins important in cell signaling and are immunomodulating agents. Cytokines include chemokines, interferons, interleukins, lymphokines, and tumor necrosis factors. An inflammatory cytokine or proinflammatory cytokine is a cytokine secreted from immune or other cells that promote inflammation. Nonlimiting examples of inflammatory cytokine s include are, interleukin-1 alpha (IL-1α), IL-1 beta (IL-1β), IL-6, IL-8, IL-12, IL-17 and IL-18, tumor necrosis factor alpha (TNF-α), interferon gamma (IFNγ), granulocyte-macrophage colony stimulating factor (GM-CSF), platelet-activating factor (PAF), macrophage migration inhibitory factor (MIF) and others. Inflammatory cytokines are predominantly produced by and involved in the upregulation of inflammatory reactions. Other inflammatory markers include glial fibrillary acidic protein (GFAP). Cytokines or their receptors to which they specifically bind may be used as a biomarker including those mentioned above.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example I—Reactive Bergmann Glia Promote Neuroinflammation and Contribute to Spinocerebellar Ataxia Pathology Through the JNK Pathway Here we describe that BG are unique among the glial population of the cerebellum in that they express abundant levels of c-Jun, a prototypical member of the Jun family of nuclear factors that is activated by phosphorylation and heterodimerizes with Fos (or ATF and CREB family members) to trigger an inflammatory cascade[28]. This uniqueness allowed us to intervene pharmacologically to tamp down BG-specific inflammation. SCA1 is used as a paradigm for these studies. SCA1 is the most severe of the polyglutamine ataxias in terms of disease progression in humans. Using SCA1 knock-in mice, we discovered that BG inflammation indeed plays a deleterious role in SCA, which can be thwarted by a c-Jun N-terminal kinase (JNK) inhibitory drug that prevents c-Jun activation. These results unequivocally establish the harmful role of BG inflammation in cerebellar degeneration and inspire the first glia-based strategy to treat the SCAs.

SCA Patients Display BG-Specific Phosphorylation of the Transcription Factor c-Jun Bacterial lipopolysaccharide (LPS) is a major component of the outer membrane of Gram-negative bacteria and is a potent inducer of inflammation. It stimulates Toll-like receptors which signal through the MAP kinase receptor family of serine/threonine kinases to result in the phosphorylation of transcription factors[29]. This signaling module culminates in the transcriptional expression of downstream inflammatory factors[30,31].

Figure 8:
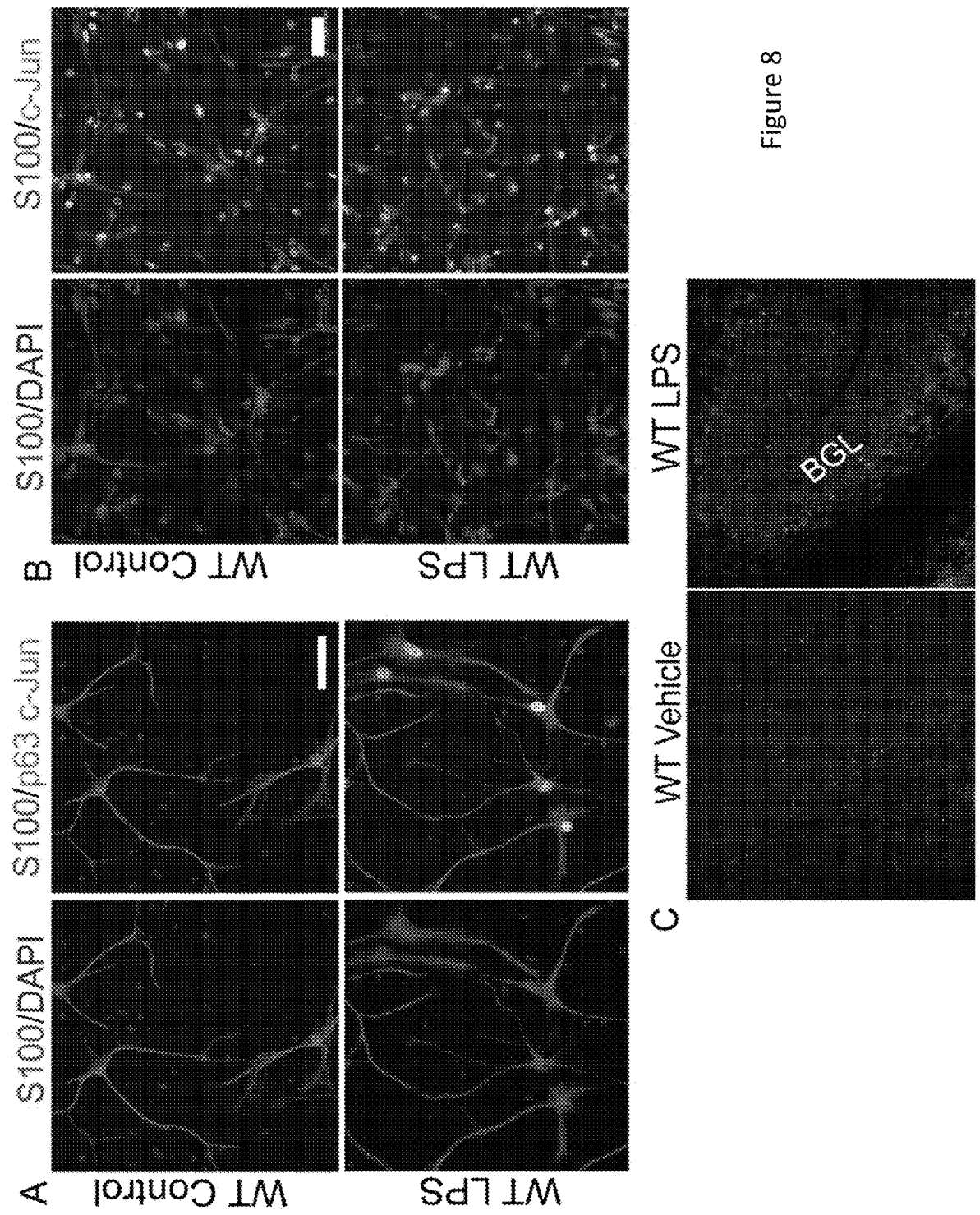
FIG. 8. Lipopolysaccharide (LPS) induces c-Jun phosphorylation in Bergmann glia in vitro and in vivo. (A) Immunostaining of S100 (red) with c-Jun-p563 (green) in DIVE (days in vitro 6) neuronal/glial cerebellar cultures generated from P4 mice and treated with PBS (control) or LPS (100 ng/mL). (B) Immunostaining of S100 (red) with total c-Jun. Slides were stained for nuclei using DAPI that labeled all the cells including glia in this mixed population. Scale bars=50 μm. (C) Immunostaining of the cerebellum for c-Jun-p563 antibody (green) in wild-type mice treated with LPS (750 m/kg) or vehicle (PBS) by intraperitoneal injection daily for 5 days.

To study cerebellar inflammation, we turned to an in vitro model system, where we treated primary mixed cerebellar cultures derived from new mouse pups with LPS. In the course of these experiments, we observed a robust phosphorylation of the inflammatory transcription factor c-Jun, a member of the MAP kinase family (FIG. 8A). This phenomenon has been previously described[32-34]. The phosphorylation of c-Jun occurs on serine 63 (c-Jun-pS63), which is known to be a target of JNK[35]. However, c-Jun phosphorylation does not occur in all cells; it is confined to a subpopulation of glial cells that we identified as BG based on co-staining with S100, a calcium binding protein that only stains these cells in the cerebellum[36]. We confirmed BG-specific c-Jun phosphorylation upon LPS induction in vivo by intraperitoneal injection of mice with LPS and staining for c-Jun-pS63 (FIG. 8B).

Since gliosis is a major feature of the SCAs, we next asked whether the SCAs mirror the LPS-induced induction of c-Jun phosphorylation specifically in BG of the cerebellum. However, the pattern of gliosis differs in the different SCAs. For instance, in most of the SCAs gliosis occurs in the cerebellum, but in SCA3 gliosis occurs mainly in the pons[37,38]. To test c-Jun activation in different SCAs, we turned to autopsy samples from patients with SCAs. We focused on SCAs 1, 2, and 7 with cerebellar gliosis and SCA3, with pontine gliosis. We observed robust phosphorylation of c-Jun in BG in SCAs 1, 2, and 7, but not SCA3 (FIG. 1). Together, these results demonstrate that BG activation as defined by c-Jun phosphorylation is a broad but not universal phenomenon across the SCAs, with the intensity of c-Jun activation corresponding to those SCAs with the most visible inflammation of BG.

Characterizing c-Jun Phosphorylation in SCA1 Mice

To delve into BG inflammation in more detail, we turned to the SCA1 knock-in model. This mouse is engineered to express ATXN1 harboring 154 glutamine repeats. While all the functions of ATXN1 have yet to be deciphered, it appears to serve a transcriptional regulator, whose functions and interactors are affected by the pathogenic expansion[39]. This is an extremely precise model of human disease since mutant ATXN1 is expressed under its endogenous promoter thus mirroring the spatial and temporal pattern of ATXN1 expression. It has also been extremely well-characterized with established timelines to monitor behavioral and pathological changes spanning the mouse lifespan[40]. It is important to note that normal ATXN1 in humans is variable but does not extend beyond 40 repeats, while mouse ATXN1 has only 2 glutamines. The maximum glutamine repeat length described in human patients is 82 and causes a childhood onset of the disease, but this repeat has to be further extended to 154 repeats to ensure a robust ataxic phenotype in the short lifespan of the mouse.

Figure 2:
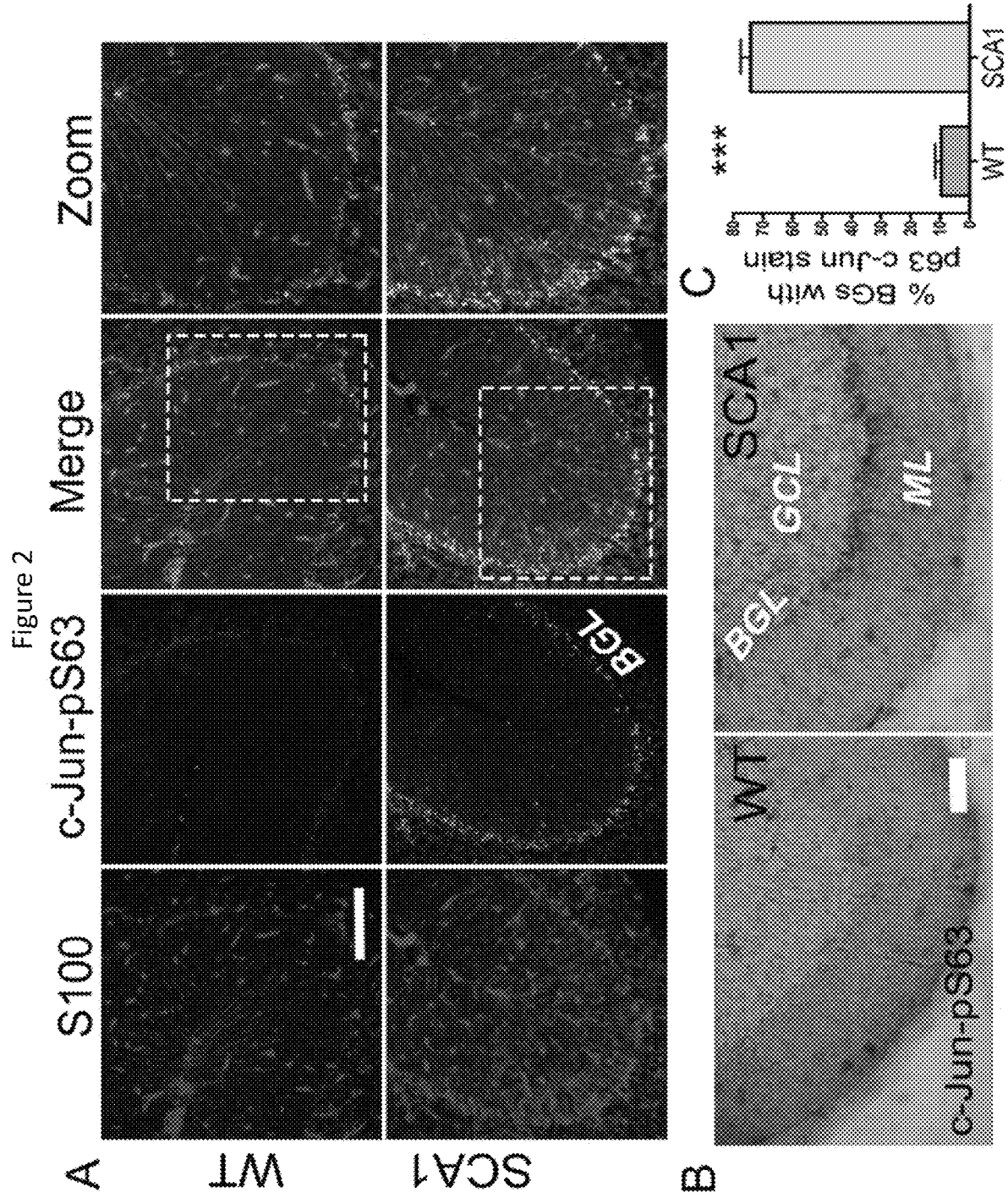
FIG. 2. c-Jun phosphorylation in the activated Bergmann glia of SCA1 mice. (A) Immunostaining of 16-week-old SCA1 mouse cerebellum with Bergmann glia (BG)-specific S100 (red) along with anti-c-Jun-p563 antibody (green). Scale bar=100 µm. White-boxed regions represent the corresponding higher-magnification images shown in the "zoom" panels. (B) HRP-based DAB immunostaining of SCA1 mouse cerebellum with anti-c-Jun-p563 antibody. Scale bar=50 µm. (C) Quantification of percentage of BG cells positive for c-Jun-p563 stain shown in panel A. (D) Immunostaining of SCA1 mouse cerebellum with total c-Jun (green). Sections are counterstained with DAPI (blue) to detect nuclei. Scale bar=100 µm. (E) Immunostaining of 16-week-old SCA1 mouse cerebellum with glia-specific GFAP antibody (green) along with calbindin antibody to detect Purkinje cells (red). Scale bar=100 µm (F) Quantification of GFAP intensity. BGL: Bergmann Glia Layer; GCL: Granular Cell Layer; ML: Molecular Layer. Sections are stained for nuclei using DAPI (blue). n=4 mice. ***P<0.001, 2-tailed unpaired Student's t test.
Figure 2:
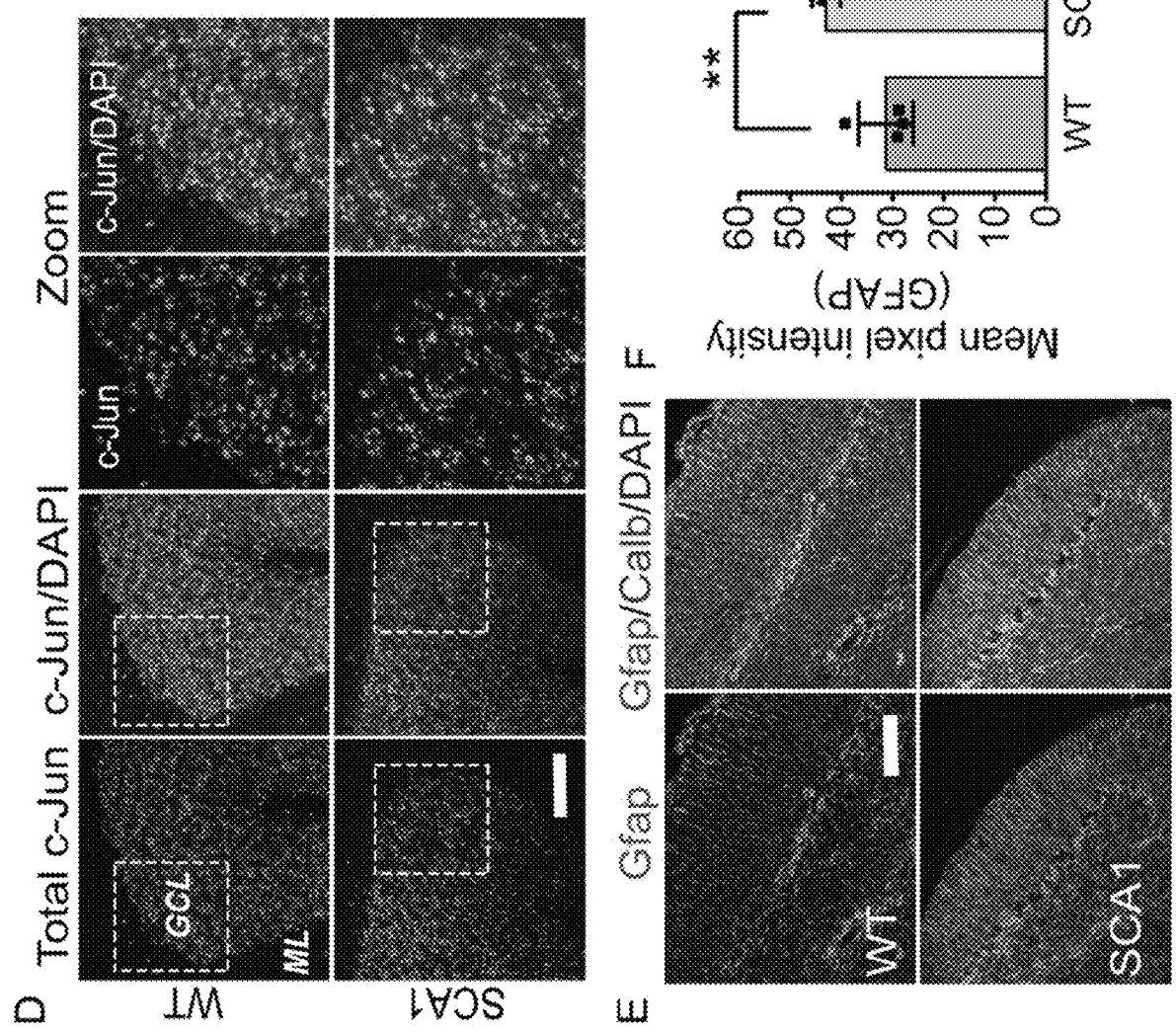

We stained for the BG-specific protein S100 along with c-Jun-pS63. The number of S100/c-Jun-pS63 double-positive cells was significantly increased in SCA1 cerebellum compared to wild-type controls (FIG. 2A-D). Phosphorylation of c-Jun was observed as early as 16 weeks of age, a time when BG also display glial activation evidenced by GFAP staining (FIG. 2E-F). These results confirm our finding of BG-specific c-Jun activation observed in human autopsy samples.

Figure 9:
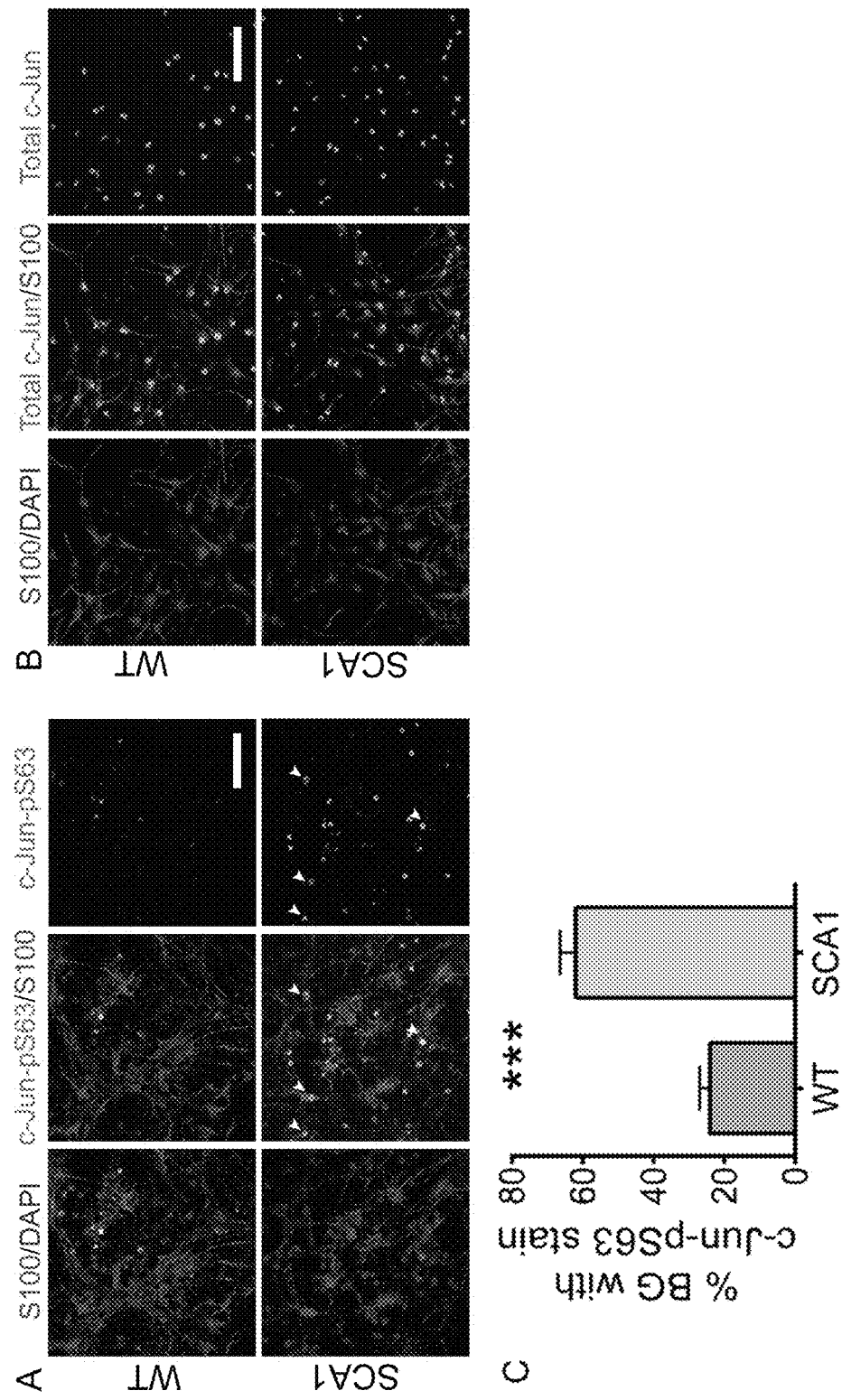
FIG. 9. (A-B) DIVE neuronal/glial cerebellar cultures generated from P4 SCA1 or wild-type mice and immunostained with S100 (red) either with (A) c-Jun-pS63 (left panels, green) or (B) total c-Jun (right panels, green). White arrow head indicates the 5100/c-Jun-pS63 double positive cells. Scale bar=100 (C) Quantification of S100/c-Jun-p563 double positives shown in panels A. n=3 individual cultures. ***P<0.001.

We also confirmed elevated c-Jun phosphorylation specifically in BG in cerebellar dissociated cultures from SCA1 postnatal mice compared to cultures derived from wild-type mice (FIG. 9).

JNK Inhibitor Treatment in SCA1 Mice Abolishes c-Jun Phosphorylation and Inhibits the Levels of the Cytokine IL-1β

Since there are well-characterized inhibitors of JNK catalytic activity, we turned to a pharmacological approach to inhibit JNK kinases. Encoded by three distinct genes, JNK kinases exist as three types: JNK 1, 2, and 3, each with further sub-types resulting from differential splicing[41]. As we yet do not know which JNK subtype is responsible for c-Jun activation in BG, we turned to a broad JNK inhibitor, SP600125 (inhibits JNK1 and 2 with an $IC_{50}$ of 40 nM, and JNK3 with an $IC_{50}$ of 90 nM)[42]. This compound crosses the blood-brain barrier and has been used to study the role of JNK kinases in the CNS[43-45].

Figure 3:
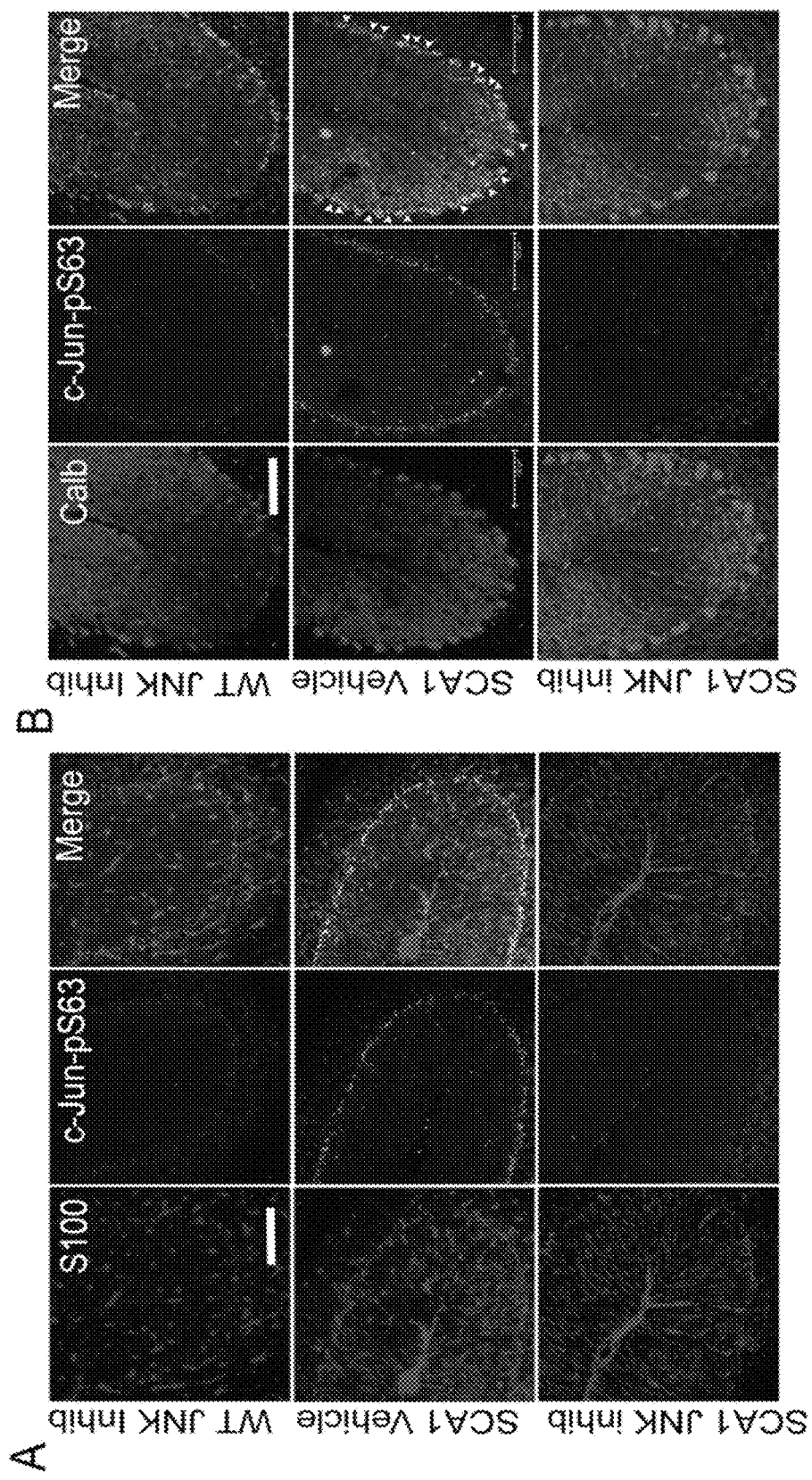
FIG. 3. Treatment of SCA1 mice with JNK inhibitor abolishes c-Jun phosphorylation in reactive Bergmann glia. (A) Immunostaining of WT (JNK inhibitor) and SCA1 (Vehicle/JNK inhibitor) treated cerebellum with Bergmann glia (BG)-specific S100 (red) along with c-Jun-p563 antibody (green). Scale bar=100 µm. (B) Immunostaining of WT (JNK inhibitor) and SCA1 (Vehicle/JNK inhibitor) treated cerebellum with Purkinje cell-specific calbindin (Calb) antibody along with c-Jun-p563 antibody. C-Jun-p563-positive BG cells (green) sit adjacent to the Purkinje cells (red). Scale bar=100 µm. (C) Immunostaining of WT (JNK inhibitor) and SCA1 (Vehicle/JNK inhibitor) treated cerebellum with glia-specific GFAP antibody (red). Sections were also stained for nuclei using DAPI (blue). Scale bar=100 µm. (D) Quantification of the percentage of BG cells positive for c-Jun-pS63, as shown in panel A. (E) Quantification of GFAP fluorescence intensity shown in panel C. n=4 mice. *P<0.05; **P<0.01, one-way ANOVA with Bonferroni's multiple comparison test. SP=JNK inhibitor SP600125, Inhib=Inhibitor.
Figure 3:
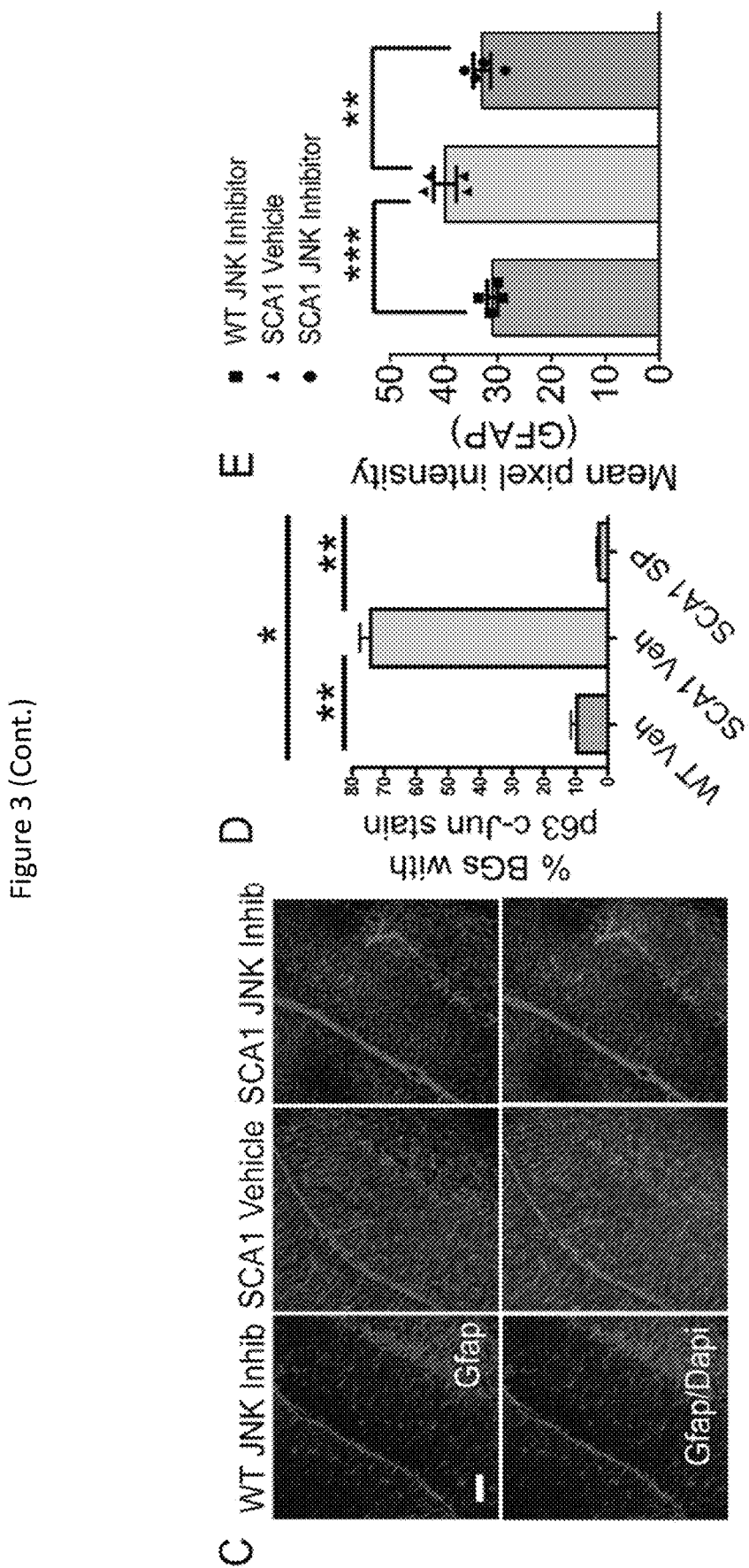

We treated SCA1 mice and wild-type littermates with intraperitoneal injections of SP600125 using a previously established delivery schedule[43-45]. As expected, treating mice with this drug caused a decrease in c-Jun phosphorylation in the BG layer (FIGS. 3A, B and D). This inhibition was accompanied by a reduction of the glial activation marker GFAP, demonstrating that JNK activation is required for BG activation (FIGS. 3C and E).

Figure 4:
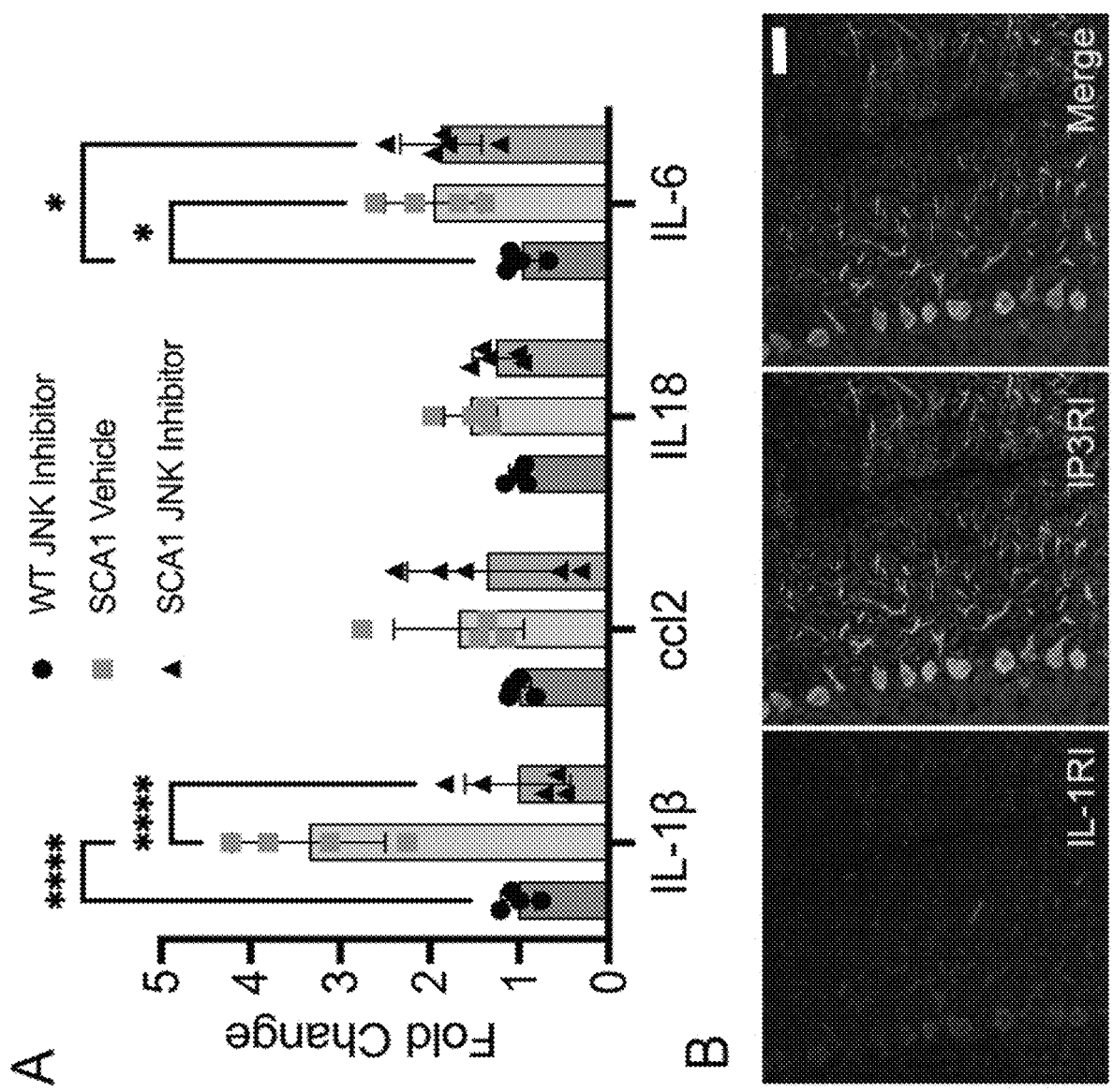
FIG. 4. JNK/c-Jun pathway is essential for Bergmann glia-specific cytokine release in SCA1 mice. (A) Quantitative real-time PCR analysis of IL-1β, IL-6, CCL2, and IL-18—four major proinflammatory cytokines from SCA1/WT cerebellum either treated with vehicle or JNK inhibitor as indicated in the bar graph legend. The data were normalized to GAPDH mRNA and are represented as the fold change. (B) Immunostaining of WT cerebellum using IL-1 receptor (IL-1RI) antibody (red) along with Purkinje cell-specific antibody against inositol-triphosphate receptor type I (IP3RI; green). Sections were also stained for nuclei using DAPI (blue). Scale bar=50 µm. n=3 mice. *P<0.5; ****P<0.0001, two-way ANOVA with Tukey's multiple comparisons test.

Since a major consequence of glial activation is cytokine release, we next asked whether the reduction of BG glial activation is associated with the reduction of any cytokines. We isolated RNA from experimental and control mice and performed real-time PCR (RT-PCR) to monitor the expression levels of IL-1β, IL-6, CCL2, and IL-18—four major proinflammatory molecules previously shown to be expressed in mice upon LPS treatment[46-47]. We observed a significant increase in levels of IL-1β and IL-6 in SCA1 mice compared to wild-type controls (3.5-fold and 2-fold, respectively). Of these, the increase in IL-1β mRNA but not IL-6 was reversed by JNK inhibition (FIG. 4A). These results point to the inflammatory factor IL-1β but not IL-6 as a BG-specific cytokine that is released upon activation.

To identify which cells would be most affected by BG-specific release of IL-1β, we performed immunostaining of cerebellum for interleukin-1 receptor type I (IL-1RI) the predominant receptor for IL-1βligand in the CNS. IL-1RI staining is not widespread in the cerebellum. We found the expression of this receptor in the cerebellum to be narrowly restricted to PCs (FIG. 4B). Taken together, our results suggest a scenario wherein IL-1β released by BG in SCA1 acts on PCs to cause neuronal dysfunction and death.

JNK Inhibition Ameliorates the SCA1 Phenotype

Figure 5:
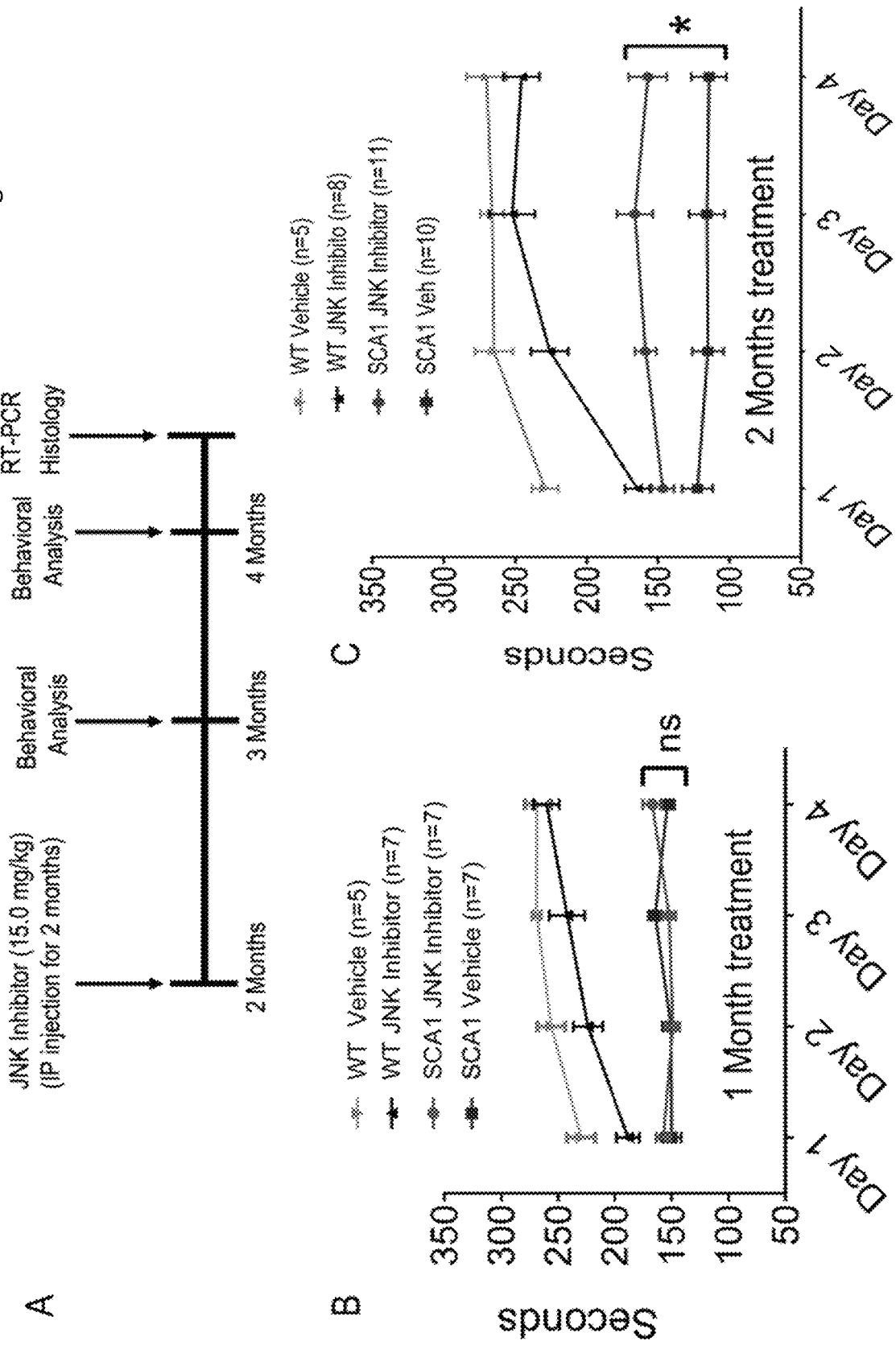
FIG. 5. Treatment of SCA1 mice with JNK inhibitor ameliorates the motor coordination impairment. (A) Schematic representation of treatment and assessment course. Mice were treated with either 15 mg/kg of JNK inhibitor or vehicle (10% DMSO and 90% corn oil) intraperitoneally (IP) until 4 months of age starting from 2 months. Then mice were rested for behavioral assays followed by pathological and quantitative RT-PCR analysis. (B and C) Rotarod performance of mice at (B) three months and (C) four months of age. (D) Mouse weight before IP administration (at 2 months of age) and following administration at 3 and 4 months of age. The number of animals used is shown in the histogram legends. *P<0.05; **P<0.01, two-way ANOVA with Bonferroni's multiple comparisons test.
Figure 5:
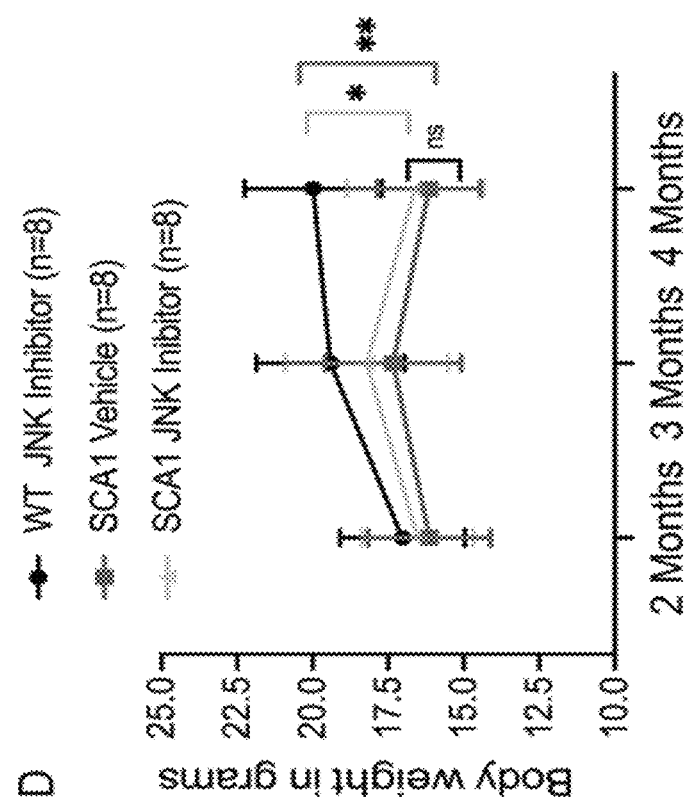

Neuroinflammation, including that caused by the release of cytokines such as IL-1β, can be either neuroprotective or deleterious in a broad range of neurological conditions including the ataxias[48,49]. To address the role of JNK activation, we studied the behavioral and pathological consequences of pharmacological inhibition of JNK in mice (FIG. 5A). For behavioral analysis, we turned to rotarod testing, a robust measure of cerebellar motor learning which distinguishes SCA1 mice from their wild-type littermates. SCA1 mice treated with JNK inhibitor showed a significant improvement in their performance; however, this improvement occurred only after a month post-treatment (n=11; *P<0.05 two months post treatment) (FIGS. 5B and C). These findings suggest that the improvement occurs because of the neuroprotective effects of inhibiting inflammation. This improvement did not extend to non-cerebellar phenotypes; for instance, the weight loss in SCA1 mice, a result of neuromuscular wasting from spinal cord involvement, was not improved by the drug (FIG. 5D).

Figure 6:
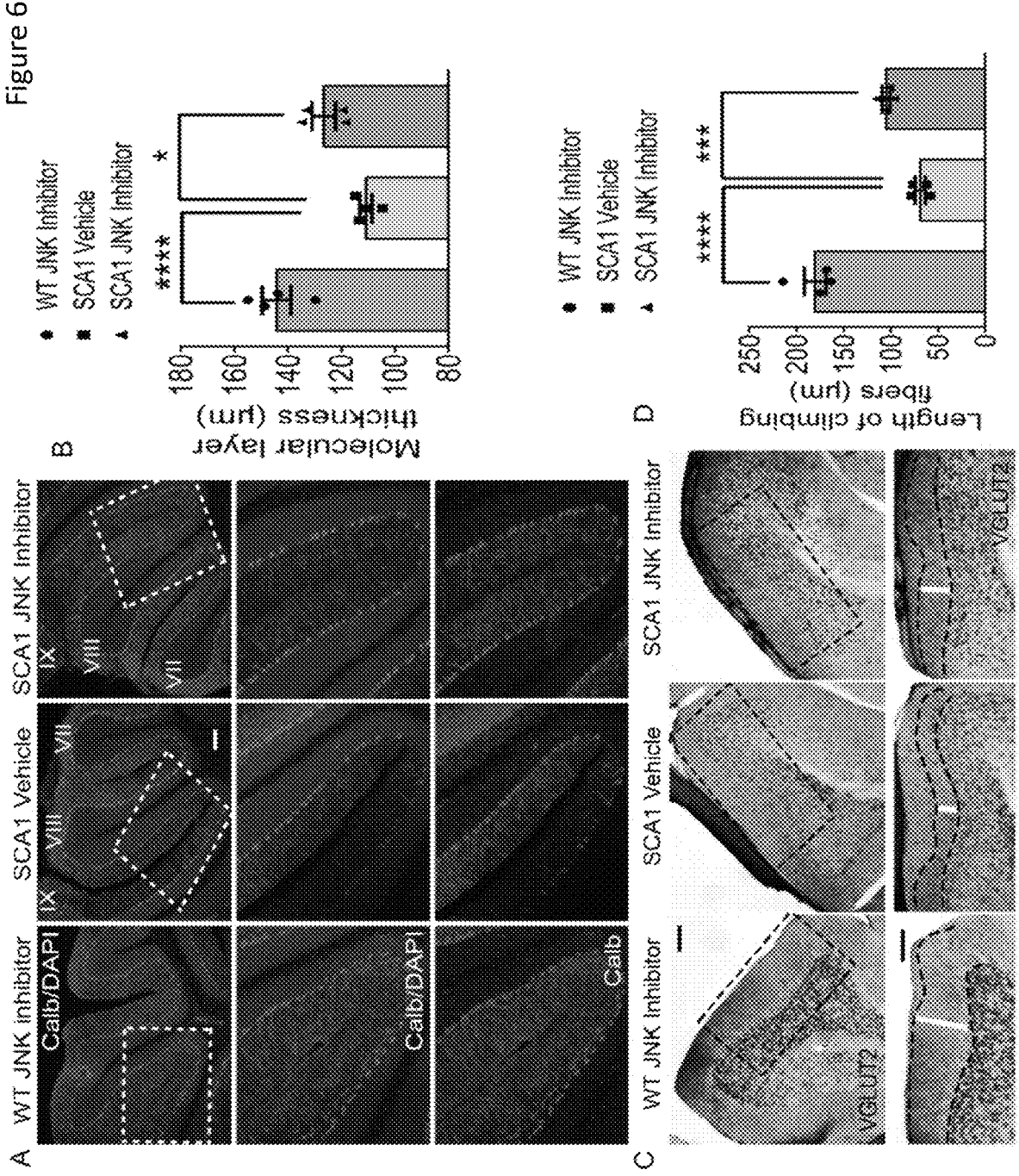
FIG. 6. JNK inhibitor treatment improves Purkinje cell pathology in SCA1 mice. (A) Cerebellar slices from 4-month-old mice treated with either JNK inhibitor or vehicle were stained with calbindin antibody specific for Purkinje cells (red). Images are taken from same lobules (VII, VIII and IX) in each condition. White-boxed regions represent the corresponding higher-magnification images shown below each panel. Sections were also stained for nuclei using DAPI (blue). Scale bar=100 µm. (B) Quantification of molecular layer thickness (Red). (C) Cerebellar slices from 4-month-old mice treated with either JNK inhibitor or vehicle were stained with vesicular glutamate transporter 2 (VGLUT2) antibody to label climbing fiber synapses on Purkinje cells. Scale bar=100 µm. (D) Quantification of the length of climbing fiber synapses, measured by VGLUT2-positive fibers (length between two black dotted lines) starting from the Purkinje layer as shown by white lines in panel C of magnified image. Black-boxed regions represent the corresponding higher-magnification images shown alongside. n=4 mice. *P<0.05; *P<0.001; **P<0.0001, one-way ANOVA with Bonferroni's multiple comparison test.

To study SCA1 cerebellar pathology, we performed experiments to address the health of PCs and their connections[50-52]. Staining for calbindin, a standard marker for PCs, we observed a significant increase in the thickness of the cerebellar molecular layer in SCA1 mice treated with the JNK inhibitor compared to mice treated with vehicle control (FIG. 6A-B). SCA1 mice also displayed a disruption in climbing fiber extension along PC dendrites, as detected by staining for the postsynaptic climbing fiber terminal marker vesicular glutamate transporter 2 (VGLUT2). This phenomenon was also improved with JNK inhibitor treatment in SCA1 mice (FIG. 6C-D).

Figure 7:
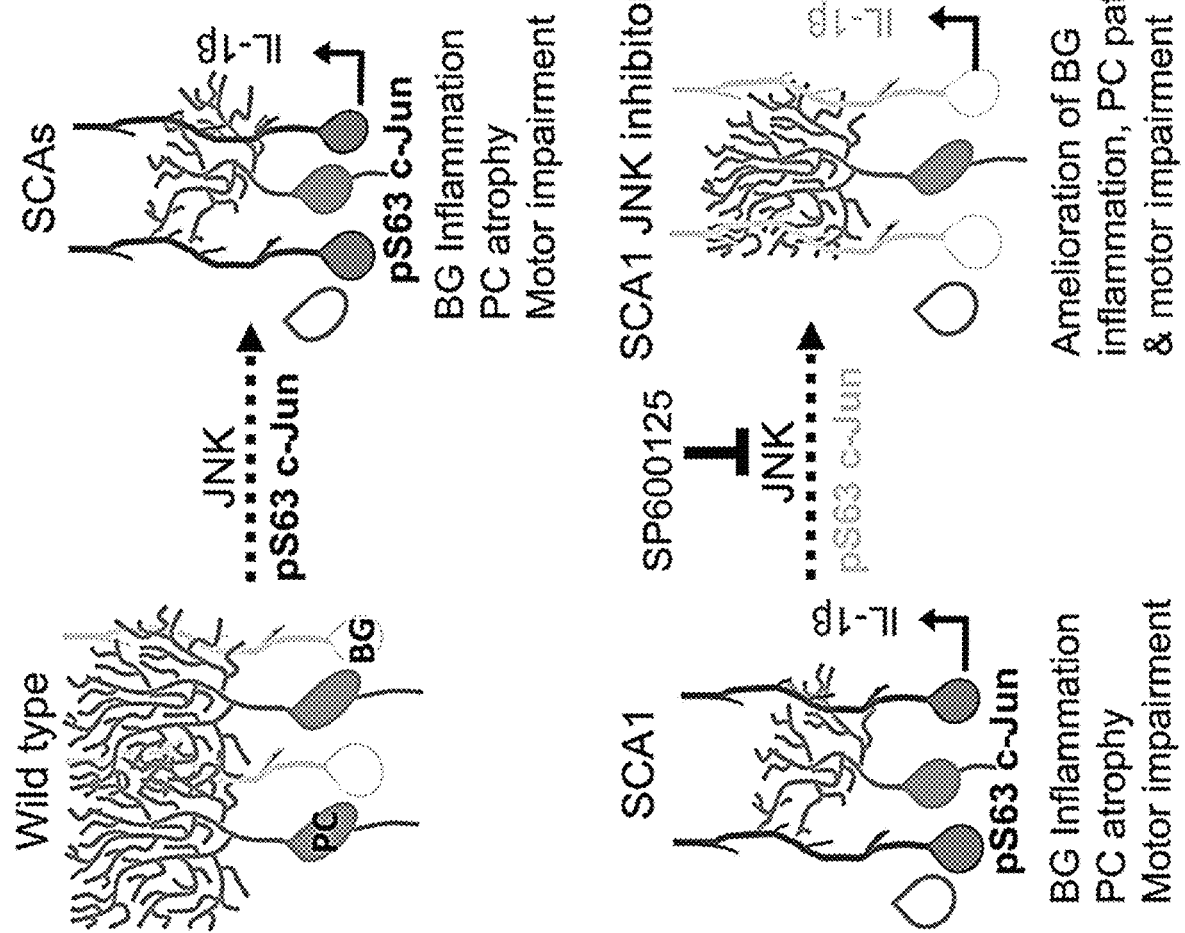
FIG. 7. Model of targeting Bergmann glia activation to combat SCAs. Top panel: SCA patients and mouse cerebellums exhibit Bergmann glia (BG)-specific JNK dependent c-Jun phosphorylation (black nuclei); the time when BG are known to have a reactive state is marked by enhanced GFAP intensity (red processes). These reactive BG release the enhanced proinflammatory cytokine IL-1β into the cerebellum in a JNK-dependent manner. Bottom panel: Treatment of SCA1 mice with JNK inhibitor SP600125 abolishes the c-Jun phosphorylation in BG (light gray nuclei) and thereby tamps down the reactive GFAP staining and cytokine IL-1β release in the cerebellum. These changes in inflammation lead to improvement in Purkinje cell pathology (green) and rescue the motor coordination impairment.

Overall, our results point to a model where BG-specific inflammation, mediated by JNK kinase, results in the release of cytokines such as IL-1β, which is deleterious to PCs. This process is ameliorated by JNK kinase inhibition, which in turn improves the SCA1 phenotype (FIG. 7).

SUMMARY

Neuroinflammation is a complex process reflecting an aggregate of interactions between glia, neurons, and the microvasculature. Some of these interactions are homeostatic and designed to be neuroprotective while others are deleterious and contribute to pathogenicity[53,54]. Dissecting and identifying these pathways in a cell type-specific manner will be crucial to finding therapies for patients suffering from neurodegeneration.

Here we describe a signaling pathway in SCAs that is defined by BG-specific phosphorylation of c-Jun. BG are particularly well-placed to play a role in Purkinje cell dysfunction and degeneration. BG outnumber PCs at a ratio of approximately 8:1; they extend fine protrusions that cover the dendritic neuropil of PCs, and they are intimately connected to their function[24,55,56]. The fortuitous observation of c-Jun phosphorylation in activated BG allowed us to test the relevance of BG inflammation in the context of the SCAs. Using SCA1 as a model, we discovered that BG inflammation can be tamped down by inhibiting JNK proteins which are responsible for catalyzing this signaling pathway and, in turn, ameliorate the disease.

As we demonstrate here, one likely mechanism for downstream toxicity of BG activation is the release of cytokines, such as IL-1β, under the control of JNK signaling. Indeed, direct injection of IL-1β into the cerebellum of wild-type mice is sufficient to induce Purkinje cell pathology and cerebellar ataxia[57]. We envisage, however, that IL-1β release is probably not the only pathological process emanating from activated BG. BG inflammation could also affect the normal housekeeping functions critical for maintaining neuronal health. For instance, BG are known to express the glutamate transporter EAAT2 (GLAST), which is responsible for the active reuptake of glutamate at excitatory synapses; this in turn modulates neurotransmission and prevents excitotoxicity. BG also express potassium Kir 4.1 channels, by which they regulate extracellular potassium levels in the vicinity of PCs and thus further fine-tune synaptic activity[22,58]. A combination of these and potentially other glial functions that play a role in neuronal health could further contribute to neuronal dysfunction. Perturbation of some of these normal homeostatic functions has already been hinted at in the SCAs. In conditional mouse models of SCA7, for example, BG-specific expression of mutant ATXN7 is sufficient to cause non-cell-autonomous PC degeneration by reducing the protein GLAST and causing morphological consequences of excitotoxicity[59]. While similar conditional studies have yet to be performed for any of the other SCAs, SCA1 mice show a reduction in the number of BG[60], with individual glia expressing less GLAST[61]. Regardless, the importance of BG to PC function has been most vividly demonstrated by optogenetic manipulation of BG, where BG inactivation leads to virtually instantaneous alterations of PC firing and subsequent cerebellar behavioral deficits[62,63].

The Examples described herein establish a treatment strategy for neurodegenerative disease and disorders, such as SCAs, with the use of JNK kinase inhibitors. These results also demonstrate that interfering with downstream targets of c-Jun activation, such as decreasing the levels or activity of IL-1β, are therapeutic, providing yet additional treatment avenues.

Materials and Methods

Mouse Lines

The Sca1$^{154Q/2Q}$ line was generated by inserting a small conserved region containing 154 CAG repeats of the human sequence into the mouse ATXN1 locus[40]. Animal experiments were performed in compliance with the National Institutes of Health's Guide for the Care and Use of Laboratory Animals and the Northwestern University Institutional Animal Care and Use Committee.

Primary Cultures of Cerebellar Neurons/Glial Cells

Neuronal/glial cerebellar cultures were derived from mice using an established protocol[35,68]. Isofluurane anesthetized mice were sacrificed by decapitation at post-natal day 4 (P4). The cerebella were dissected away from the meninges and choroid plexus. Minced cerebellar tissue was trypsinized for 15 min at 37° C. and then triturated in Hank's Balanced Salt Solution containing 10 U/mL DNAse I (Roche Diagnostics). The cells were centrifuged at 2,000 rpm for 7 min and resuspended in Neurobasal media (Sigma) containing 4 mM glutamine, 10% FBS, 100 U/mL Penicillin/streptomycin, and 25 mM KCl (Sigma-Aldrich). After counting, $7.5 \times 10^5$ cells were plated on precoated poly-D-lysine glass coverslips in 24-well plates. Cultures were maintained at 37° C., 5% $CO_2$, and media were changed every 2 days. On day 6 in culture, the cells were treated with LPS (Sigma #L2630) at 100 ng/mL concentration for 3 h. They were then fixed in 4% paraformaldehyde for immunohistochemical staining experiments.

In vivo LPS treatment in wild-type mice was performed as previously described[35]. Briefly, LPS in PBS was administered intraperitoneally at a dose of 750 μg/kg for seven consecutive days. The control mice received PBS as a vehicle. After seven days of injections, mice were sacrificed for the immunohistochemical analysis.

Human Brain Immunohistochemistry

We obtained the SCA autopsy samples (four SCA1, three SCA2, three SCA3, three SCA7, and four age-matched controls) from Arnulf Koeppen and Laura Ranum, with approval from the institutional review boards of the Veterans Affairs Medical Center, Albany, New York, and the University of Florida, respectively. Post-mortem cerebellar tissue from SCA patients was mounted in paraffin blocks, and 5 μm-thick slices were cut from each paraffin block, processed for HRP-DAB staining, and counterstained with hematoxylin. Antigen retrieval and antibody staining was optimized at the Northwestern University Pathology Core.

Experimental Injections with Pharmacological Agents

The JNK inhibitor SP600125 (#HY-12041, MedChemExpress) was dissolved in 10% DMSO and 90% corn oil. It was injected intraperitoneally on an alternate day schedule at a dose of 15 mg/kg starting when mice were two months of age and continuing for two months. Control mice were treated with vehicle alone. The mice were then evaluated behaviorally and pathologically in a blinded fashion. Since SCA mice do not display sex-based differences in their cerebellar phenotype, the read-outs from males and females were pooled before statistical analysis.

Rotarod Assays

Rotarod testing was performed by placing mice on a motorized rotating rod that accelerates linearly from 4 to 40 rotations per minute over a maximum duration of 5 minutes (Ugo Basile, Comerio, Italy)[14]. The time it takes for a mouse to fall off was recorded. If mice passively clung to the rod for two consecutive rotations, that was also counted as a fall. Mice were subjected to four trials per day for four consecutive days. To ensure enough recovery time between trials, animals were given 10-15 min rest between the end of a trial and the subsequent trial.

Pathological Assays/Immunohistochemistry

Mice were sacrificed by deep anesthesia (isoflurane) and transcardiac perfusion (first with PBS and then with 4% Paraformaldehyde in PBS). The brains were dissected from the cranium and post-fixed with 4% paraformaldehyde in PBS in an overnight incubation at 4° C. They were subsequently equilibrated in a 10-30% sucrose gradient and embedded in optimal cutting temperature medium. The cerebella were sliced into 30 μm-thick sections with a cryostat (Microm M505, Thermo Fisher Scientific) or Vibratome (Leica VT1000 S).

Immunohistochemistry was then performed either by immunofluorescence or horseradish peroxidase (HRP)-based 3,3'-diaminobenzidine (DAB) detection.

For immunofluorescence, the sections were permeabilized and blocked with 10% normal goat serum and 0.25% Triton X-100 in 1× Tris-buffered saline for 1 h, after which the sections were incubated with primary antibodies (diluted in 1% BSA) overnight at 4° C. The following day, the sections were washed three times with PBS, then incubated with fluorescently tagged secondary antibodies for 2 h at room temperature in the dark. Finally, the sections were washed three times with TBS (adding DAPI into the last wash) and mounted onto glass slides using Mowiol 4-88 (Sigma-Aldrich). The sections were imaged using a CTR6500 confocal microscope equipped with Leica LAS AF software (Leica, Buffalo Grove, IL).

For HRP-based DAB staining, the sections were processed for antigen retrieval using citrate-based buffer (pH 6.0) (Abcam #ab93678) and quenched for endogenous peroxidase activity by treating with 3% $H_2O_2$. The sections were then blocked in 10% normal blocking serum for 20 min, washed in PBS, and then incubated with primary antibody (diluted in 1% BSA) for 1 h. Sections were washed with PBS and incubated with biotinylated secondary antibody (rabbit IgG VECTASTAIN #PK-6101 or mouse IgG VECTASTAIN #PK-4002) for 30 min. After a wash with PBS, the sections were incubated with VECTASTAIN elite ABC reagent for 30 min followed by incubation with peroxidase substrate solution (VECTOR #SK-4100) for 2-10 min at room temperature until the desired brown color developed. Immediately, the slides were rinsed under tap water for 5 min. Slides were mounted using aqueous mounting medium (VectaMount AQ #H-5501).

Quantitative Real-Time PCR (RT-PCR)

Mice were sacrificed by deep anesthesia (isofluorane) followed by decapitation. The cerebellar tissue was dissected from the cranium. Cerebellar RNA was extracted using an RNeasy Plus Universal mini kit (Qiagen #73404), which was then used to generate cDNA using a reverse-transcription kit (Biorad #1708840). Quantitative PCR was subsequently performed using TaqMan probes with iTaq Universal Probe Supermix on a CFX96 Real-Time thermocyler (Biorad C1000 Touch). For each sample, relative levels of target gene transcript were calculated as the ratio of Ct value of target gene (experimental to control sample) normalized to similarly derived GAPDH ratios.

The probes used were as follows. IL-1b: Catalog #4331182, ID: Mm00434228_m1. CCL2: Catalog #4331182, ID: Mm00441242_m1. IL-18: Catalog #4331182, ID: Mm00434225_m1. IL-6: Catalog #331182, ID: Mm00446190_m1. GAPDH: Catalog #4352661, Mm99999915_g1. All probes were fluorescein amidite-labeled.

Antibodies

The following primary antibodies were used: rabbit anti-c-Jun mAb (#9165 Clone 60A8, Cell Signaling), rabbit anti-phospho-c-Jun (Ser63) II (#9261, Cell Signaling), mouse anti-GFAP mAb (#MCA-5C10, EnCor Biotechnology Inc), rabbit anti-GFAP (#Z0334, Dako), mouse anti-VGLUT2 mAb (#MAB5504, Millipore Sigma), mouse anti-IL-1RI (#AF771, R&D Systems), rabbit anti-IP3R-I (#PA1-901, Thermo Fisher), mouse anti-S100B mAb (#S2532, Sigma-Aldrich).

Microscopy and Image Analyses

Nikon Eclipse TE2000-E fluorescence microscopes equipped with Intensilight C-HGFI (Nikon Inc., Melville, NY, USA) were used. Epifluorescence images were acquired using a Digital Sight DS-Qi1MC CCD camera (Nikon Inc., Melville, NY, USA), and light images were acquired using a Ds-Fi1 camera (Nikon Inc., Melville, NY, USA). Confocal images were collected using Lieca TCS SP5 confocal microscopes (Leica Inc., Bensheim, Germany) and used to acquire low- and high-magnification images of fluorescent samples. Z-stacks were processed using ImageJ (NIH, Bethesda, MD, USA).

Statistical Analysis

We performed all statistical tests using GraphPad Prism 4.0 (GraphPad Software). Data is presented as mean±SEM The level of significance was set at P values less than 0.05. Two tailed t-tests were used for comparison of the two data sets while two-way ANOVA and one-way ANOVA followed by Bonferroni correction were used for experiments with three or more data sets. Molecular and biochemical analyses were performed using a minimum of three biological replicates per condition.

Example II

Spinocerebellar ataxia type 1 (SCA1) is an adult-onset neurodegenerative movement disorder caused by a pathogenic polyglutamine expansion (CAG repeat) in the protein Ataxin-1 (ATXN1). People with this condition initially experience problems with coordination and balance (ataxia).

There are precise genetic mouse models of this disease—most notably a knock-in mouse where the mouse ATXN1 locus is replaced by a cassette expressing an expanded repeat.

Using these mice, it has become clear that the main pathological hallmark of the disease is Purkinje cell loss in cerebellum. However, we have recently found that Bergmann glia—a population of glial cells—that closely surround Purkinje neurons show signs of inflammation in spinocerebellar ataxia type 1. Moreover, this inflammation is characterized by upregulation by the JNK-dependent phosphorylation of c-Jun in Bergmann glia. When JNK phosphorylation is inhibited by a JNK kinase inhibitor, phosphorylation of c-Jun is decreased, with an improvement of the pathology and behavior of SCA1 mice. These experiments set the stage for using a JNK-kinase inhibitor to treat SCA1 and by extension any neurodegenerative diseases caused by excessive JNK kinase activity.

Mutant ATXN1 Elicits JNK-Dependent Phosphorylation of c-Jun in Bergmann Glial Cells of SCA1

Using antibodies to phosphorylated c-Jun (c-Jun-pS63 specific Ab) we found that there is specific staining of Bergmann glia in SCA1 mice compared to controls (Bergmann glia are identified by staining with the glial marker S100) (FIG. 2A).

Next we isolated the Bergmann glial cells from the SCA1 and WT cerebellum and performed double staining as previously mentioned. Isolated SCA1 Bergmann Glia are enriched with the c-Jun phosphorylation compared to WT BGs, suggesting the inflammation in BGs is a cell autonomous event (FIG. 9A).

Figure 10:
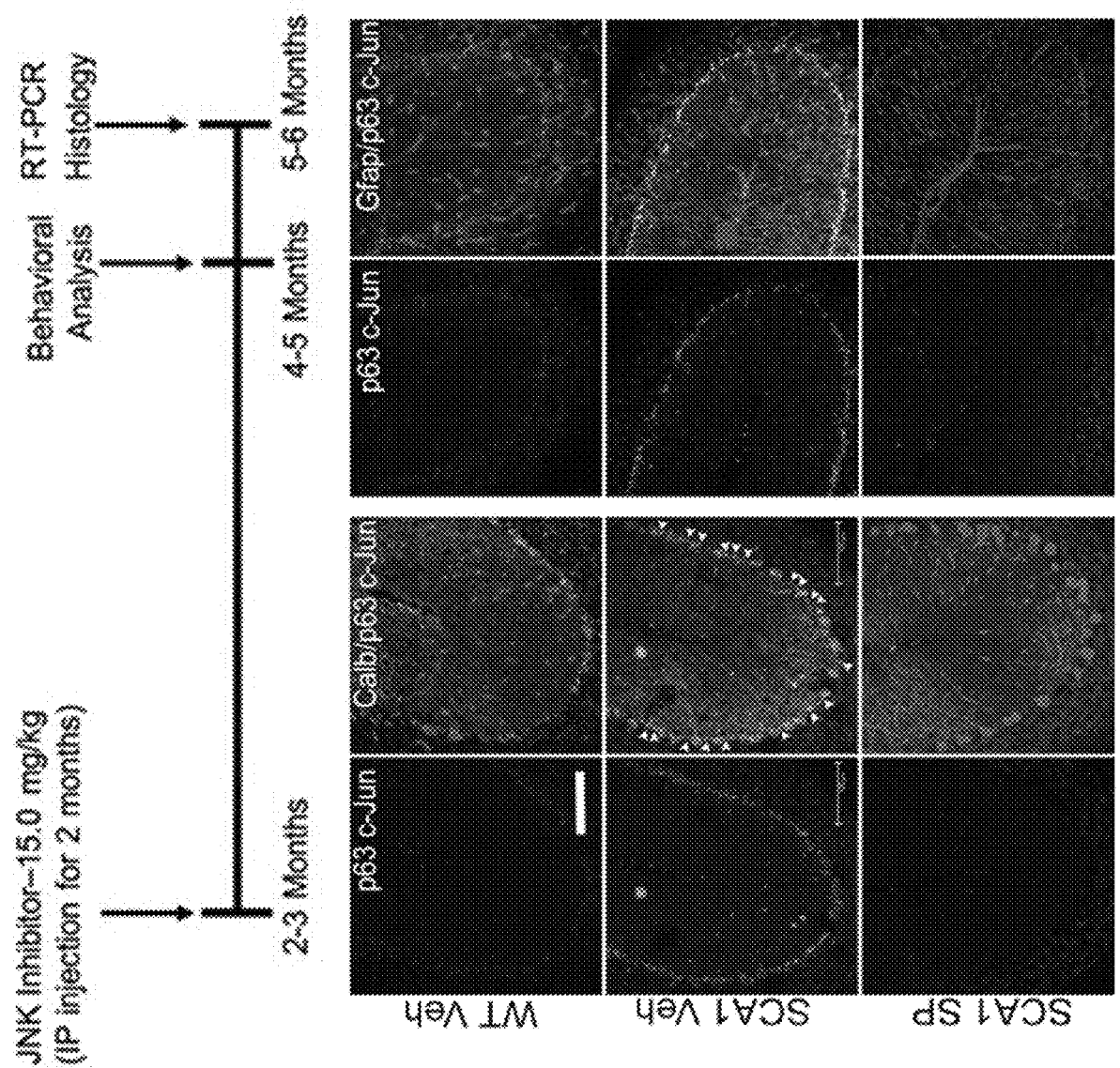
FIG. 10. Abrogation of c-Jun phosphorylation upon SP600125 treatment in SCA1. Double saining of S100 or Calbindin with c-Jun p63 antibody in 5-6 months old SCA1/WT cerebellum (Top). SCA1 Bergmann glia evident with absence of c-Jun phosphorylation upon JNK inhibitor treatment.

JNK Inhibitor Treatment Abrogate the c-Jun Phosphorylation from Bergmann Glial Cells As the c-Jun N-terminal kinase (JNK) is the major kinase mediating c-Jun transactivation by phosphorylation at S63 site, we examined the effect of the JNK-specific inhibitor SP600125 (MedChemExpress #129-56-6) on c-Jun phosphorylation. We treated SCA1 mice with the JNK-specific inhibitor for two months by injecting intraperitonially. We found that SP600125 clearly abolished the increase of S100/c-Jun-p563 staining in Bergmann glial cells. We also confirmed the findings with double staining of S100/Calbindin, to show indeed the S63 phosphorylation staining marks the Bergmann glial cell body that resides adjacent to the Purkinje cell body (FIG. 10).

Taken together, these results establish that the mutant ATXN1 directly activates Bergmann glial cells and in turn elicits JNK-dependent transactivation of c-Jun.

JNK Inhibitor Treatment Improves the Motor Coordination in SCA1 Mice

Figure 11:
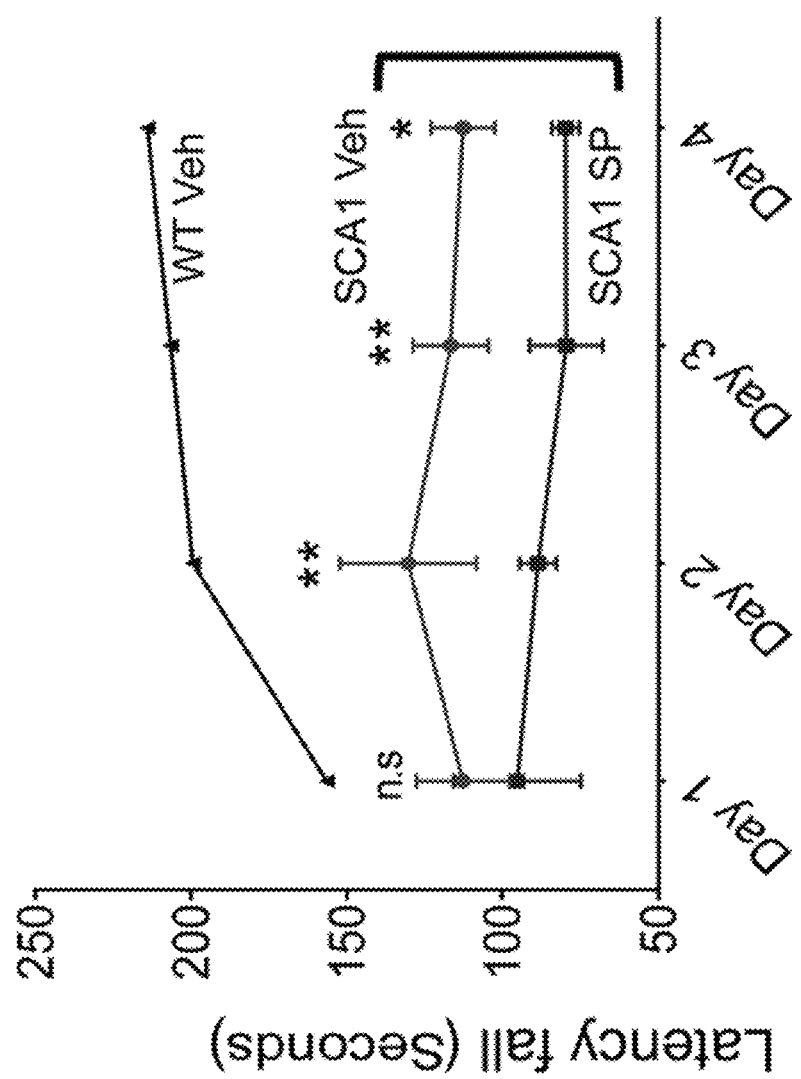
FIG. 11. JNK inhibitor treatment improves the motor co-ordination in SCA1 mice. Rotarod assay of SCA1/WT treated either with SP600125 or Vehicle treatment.

Next, we checked for ataxia phenotype (loss of motor control and balance) using accelerating rotating rod (rotarod). In rotarod test; mice that have cerebellar deficits tend to fall off the rotarod early as it accelerates; the time it takes for a mouse to fall is recorded (latency to fall). The mice treated with JNK inhibitor—SP600125 demonstrated improved performance on rotarod when compared to vehicle treated SCA1 mice (FIG. 11), suggesting the inhibition of c-Jun phosphorylation normalized the inflammatory factor release in cerebellum and ameliorate the motor symptom in SCA1 mice.

Figure 12:
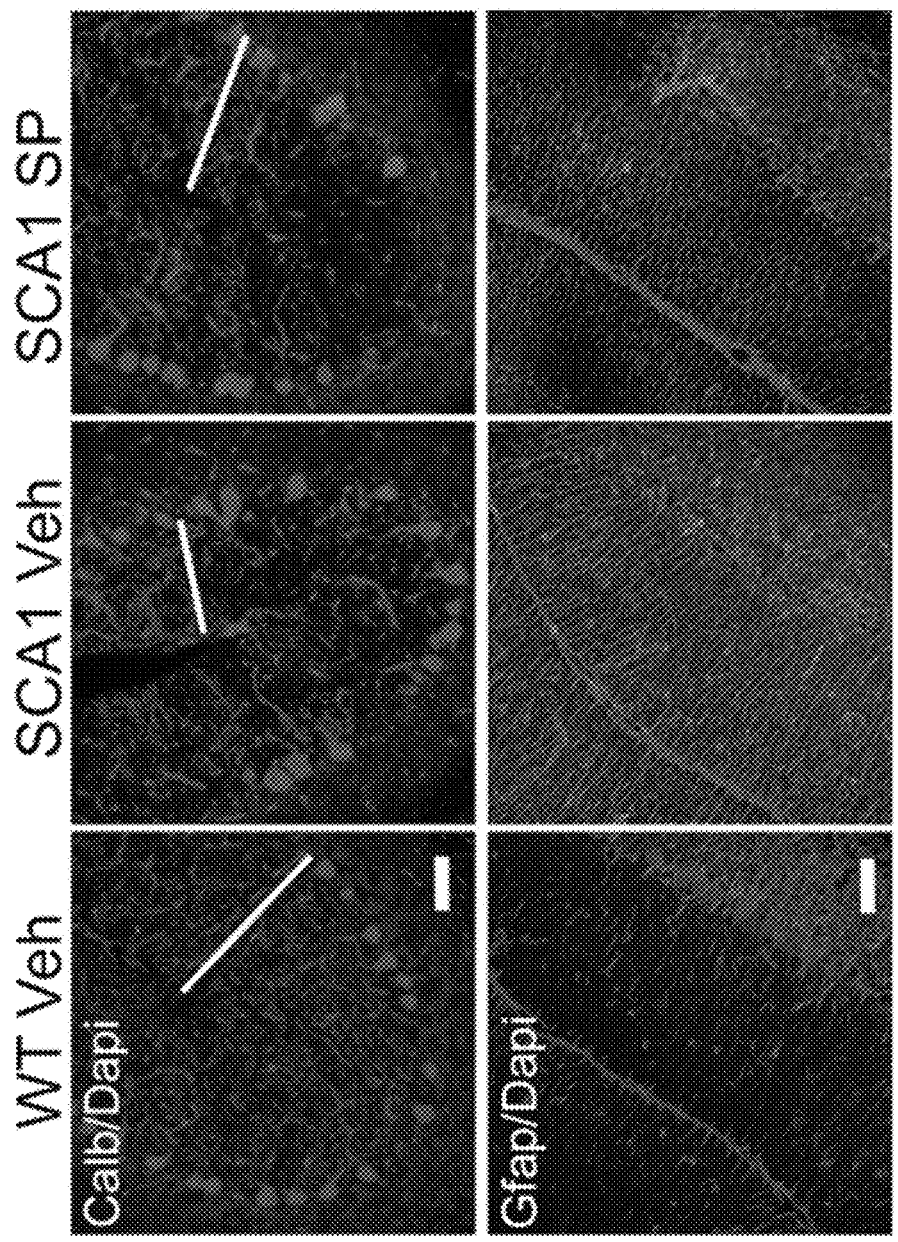
FIG. 12. JNK inhibitor treatment improves the Purkinje cell and Bergmann glial pathology. SCA1/WT mice treated either with SP600125 or Vehicle. Immunostaining of cerebellum with either calbindin to assess the molecular layer width or with GFAP to assess the Bergmann glial inflammation phenotype.

Treatment of SCA1 Mice with JNK Inhibitor Improves the Bergmann Glial and Purkinje Cell Pathology Next we investigated whether SP600125 treatment ameliorates the cerebellar pathology characteristic feature of SCA1, including Purkinje cell dendritic atrophy—can be quantified as a decrease in the width of molecular layer in cerebellar slices stained with the Purkinje cell marker calbindin (FIG. 12). As seen in figure, there was a significant reduction in molecular layer thickness in SCA1 mice treated with vehicle when compared to WT mice treated with vehicle, suggesting that the Purkinje cell dendritic arbors are degenerating. There is significant improvement in molecular layer thickness in SP600125 treated SCA1 mice compared to that of vehicle treated mice.

We also checked for the Bergmann glial reactive phenotype by staining with GFAP antibody, where the upregulation of GFAP staining indicates the reactive status of glial phenotype. Vehicle treated SCA1 show significant upregulation of GFAP staining compared to that of WT. Treatment with JNK inhibitor ameliorates the reactive phenotype with clear down regulation of GFAP staining in Bergmann glial layer.

There results establish that the JNK inhibitor treatment is able to reduce the inflammation in cerebellum and thereby rescues the SCA1 disease phenotype.

REFERENCES

1 Diallo, A. et al. Survival in patients with spinocerebellar ataxia types 1, 2, 3, and 6 (EUROSCA): a longitudinal cohort study. *The Lancet. Neurology* 17, 327-334, doi:10.1016/s1474-4422(18)30042-5 (2018).

2 Klockgether, T., Mariotti, C. & Paulson, H. L. Spinocerebellar ataxia. *Nat Rev Dis Primers* 5, 24, doi:10.1038/s41572-019-0074-3 (2019).

3 Ashizawa, T., Öz, G. & Paulson, H. L. Spinocerebellar ataxias: prospects and challenges for therapy development. *Nat Rev Neurol* 14, 590-605, doi:10.1038/s41582-018-0051-6 (2018).

4 Sullivan, R., Yau, W. Y., O'Connor, E. & Houlden, H. Spinocerebellar ataxia: an update. *Journal of Neurology* 266, 533-544, doi:10.1007/s00415-018-9076-4 (2019).

5 Park, J. Y., Joo, K. & Woo, S. J. Ophthalmic Manifestations and Genetics of the Polyglutamine Autosomal Dominant Spinocerebellar Ataxias: A Review. *Front Neurosci* 14, 892, doi:10.3389/fnins.2020.00892 (2020).

6 Klockgether, T., Mariotti, C. & Paulson, H. L. Spinocerebellar ataxia. *Nature Reviews Disease Primers* 5, 24, doi:10.1038/s41572-019-0074-3 (2019).

7 Edamakanti, C. R., Do, J., Didonna, A., Martina, M. & Opal, P. Mutant ataxin1 disrupts cerebellar development in spinocerebellar ataxia type 1. *J Clin Invest* 128, 2252-2265, doi:10.1172/jci96765 (2018).

8 Ebner, B. A. et al. Purkinje Cell Ataxin-1 Modulates Climbing Fiber Synaptic Input in Developing and Adult Mouse Cerebellum. *The Journal of Neuroscience* 33, 5806-5820, doi:10.1523/jneurosci.6311-11.2013 (2013).

9 Binda, F., Pernaci, C. & Saxena, S. Cerebellar Development and Circuit Maturation: A Common Framework for Spinocerebellar Ataxias. *Frontiers in neuroscience* 14, 293-293, doi:10.3389/fnins.2020.00293 (2020).

10 Robinson, K. J., Watchon, M. & Laird, A. S. Aberrant Cerebellar Circuitry in the Spinocerebellar Ataxias. *Front Neurosci* 14, 707, doi:10.3389/fnins.2020.00707 (2020).

11 Sheeler, C. et al. Glia in Neurodegeneration: The Housekeeper, the Defender and the Perpetrator. *Int J Mol Sci* 21, doi:10.3390/ijms21239188 (2020).

12 Stevenson, R., Samokhina, E., Rossetti, I., Morley, J. W. & Buskila, Y. Neuromodulation of Glial Function During Neurodegeneration. *Frontiers in Cellular Neuroscience* 14, doi:10.3389/fncel.2020.00278 (2020).

13 Gleichman, A. J. & Carmichael, S. T. Glia in neurodegeneration: Drivers of disease or along for the ride? *Neurobiology of Disease* 142, 104957, doi:http://doi.org/10.1016/j.nbd.2020.10.104957 (2020).

14 Hu, Y. S. et al. Self-assembling vascular endothelial growth factor nanoparticles improve function in spinocerebellar ataxia type 1. *Brain*, doi:10.1093/brain/awy328 (2019).

15 Cvetanovic, M., Ingram, M., Orr, H. & Opal, P. Early activation of microglia and astrocytes in mouse models of spinocerebellar ataxia type 1. *Neuroscience* 289, 289-299, doi:10.1016/j.neuroscience.2015.01.003 (2015).

16 Cvetanovic, M., Patel, J. M., Marti, H. H., Kini, A. R. & Opal, P. Vascular endothelial growth factor ameliorates the ataxic phenotype in a mouse model of spinocerebellar ataxia type 1. *Nat Med* 17, 1445-1447, doi:10.1038/nm.2494 (2011).

17 Zahr, N. M., Mayer, D., Rohlfing, T., Sullivan, E. V. & Pfefferbaum, A. Imaging neuroinflammation? A perspective from MR spectroscopy. *Brain Pathol* 24, 654-664, doi:10.1111/bpa.12197 (2014).

18 Joers, J. M. et al. Neurochemical abnormalities in premanifest and early spinocerebellar ataxias. *Annals of neurology* 83, 816-829, doi:10.1002/ana.25212 (2018).

19 Schuster, K. H. et al. Impaired Oligodendrocyte Maturation Is an Early Feature in SCA3 Disease Pathogenesis. *J Neurosci* 42, 1604-1617, doi:10.1523/jneurosci.1954-20.2021 (2022).

20 Tejwani, L. et al. Longitudinal single-cell transcriptional dynamics throughout neurodegeneration in SCA1. *bioRxiv*, 2021.2010.2022.465444, doi:10.1101/2021.10.22.465444 (2021).

21 Ferro, A., Sheeler, C., Rosa, J. G. & Cvetanovic, M. Role of Microglia in Ataxias. *Journal of molecular biology* 431, 1792-1804, doi:10.1016/j.jmb.2019.01.016 (2019).

22 Kim, J. H., Lukowicz, A., Qu, W., Johnson, A. & Cvetanovic, M. Astroglia contribute to the pathogenesis of spinocerebellar ataxia Type 1 (SCA1) in a biphasic, stage-of-disease specific manner. *Glia* 66, 1972-1987, doi:10.1002/glia.23451 (2018).

23 Qu, W. et al. Inhibition of colony-stimulating factor 1 receptor early in disease ameliorates motor deficits in SCA1 mice. *J Neuroinflammation* 14, 107, doi:10.1186/s12974-017-0880-z (2017).

24 Buffo, A. & Rossi, F. Origin, lineage and function of cerebellar glia. Prog Neurobiol 109, 42-63, doi:10.1016/j.pneurobio.2013.08.001 (2013).

25 Leung, A. W. & Li, J. Y. H. The Molecular Pathway Regulating Bergmann Glia and Folia Generation in the Cerebellum. *Cerebellum* 17, 42-48, doi:10.1007/s12311-017-0904-3 (2018).

26 Tan, Y.-L., Yuan, Y. & Tian, L. Microglial regional heterogeneity and its role in the brain. *Molecular Psychiatry* 25, 351-367, doi:10.1038/s41380-019-0609-8 (2020).

27 Hayashi, C., Suzuki, N., Takahashi, R. & Akazawa, C. Development of type I/II oligodendrocytes regulated by teneurin-4 in the murine spinal cord. *Scientific Reports* 10, 8611, doi:10.1038/s41598-020-65485-0 (2020).

28 Grondin, B. et al. c-Jun homodimers can function as a context-specific coactivator. *Mol Cell Biol* 27, 2919-2933, doi:10.1128/mcb.00936-06 (2007).

29 Miyake, K. Innate recognition of lipopolysaccharide by Toll-like receptor 4-MD-2. *Trends Microbiol* 12, 186-192, doi:10.1016/j.tim.2004.02.009 (2004).

30 Jin, J. J., Kim, H. D., Maxwell, J. A., Li, L. & Fukuchi, K. Toll-like receptor 4-dependent upregulation of cytokines in a transgenic mouse model of Alzheimer's disease. *J Neuroinflammation* 5, 23, doi:10.1186/1742-2094-5-23 (2008).

31 Ngkelo, A., Meja, K., Yeadon, M., Adcock, I. & Kirkham, P. A. LPS induced inflammatory responses in human peripheral blood mononuclear cells is mediated through NOX4 and Gia dependent PI-3kinase signalling. *J Inflamm (Loud)* 9, 1, doi:10.1186/1476-9255-9-1 (2012).

32 Jang, S., Kelley, K. W. & Johnson, R. W. Luteolin reduces IL-6 production in microglia by inhibiting JNK phosphorylation and activation of AP-1. *Proc Natl Acad Sci USA* 105, 7534-7539, doi:10.1073/pnas.0802865105 (2008).

33 Waetzig, V. et al. c-Jun N-terminal kinases (JNKs) mediate pro-inflammatory actions of microglia. *Glia* 50, 235-246, doi:10.1002/glia.20173 (2005).

34 Albanito, L., Reddy, C. E. & Musti, A. M. c-Jun is essential for the induction of Il-1β gene expression in in vitro activated Bergmann glial cells. *Glia* 59, 1879-1890, doi:10.1002/glia.21244 (2011).

35 Albanito, L., Reddy, C. E. & Musti, A. M. c-Jun is essential for the induction of Il-1beta gene expression in in vitro activated Bergmann glial cells. *Glia* 59, 1879-1890, doi:10.1002/glia.21244 (2011).

36 Dooves, S. et al. Bergmann glia translocation: a new disease marker for vanishing white matter identifies therapeutic effects of Guanabenz treatment. *Neuropathology and applied neurobiology* 44, 391-403, doi:10.1111/nan.12411 (2018).

37 Evert, B. O. et al. Inflammatory genes are upregulated in expanded ataxin-3-expressing cell lines and spinocerebellar ataxia type 3 brains. *J Neurosci* 21, 5389-5396, doi:10.1523/jneurosci.21-15-05389.2001 (2001).

38 Dun, A. et al. Spinocerebellar ataxia 3 and Machado-Joseph disease: clinical, molecular, and neuropathological features. *Annals of neurology* 39, 490-499, doi:10.1002/ana.410390411 (1996).

39 Tejwani, L. & Lim, J. Pathogenic mechanisms underlying spinocerebellar ataxia type 1. *Cell Mol Life Sci* 77, 4015-4029, doi:10.1007/s00018-020-03520-z (2020).

40 Watase, K. et al. A Long CAG Repeat in the Mouse Scal Locus Replicates SCA1 Features and Reveals the Impact of Protein Solubility on Selective Neurodegeneration. *Neuron* 34, 905-919, doi: http://dx.doi.org/10.1016/S0896-6273(02)00733-X (2002).

41 Bogoyevitch, M. A. The isoform-specific functions of the c-Jun N-terminal Kinases (JNKs): differences revealed by gene targeting. *Bioessays* 28, 923-934, doi:10.1002/bies.20458 (2006).

42 Hepp Rehfeldt, S. C., Majolo, F., Goettert, M. I. & Laufer, S. c-Jun N-Terminal Kinase Inhibitors as Potential Leads for New Therapeutics for Alzheimer's Diseases. *Int J Mot Sci* 21, doi:10.3390/ijms21249677 (2020).

43 Wang, W. et al. SP600125, a new JNK inhibitor, protects dopaminergic neurons in the MPTP model of Parkinson's disease. *Neurosci Res* 48, 195-202, doi:10.1016/j.neures.2003.10.012 (2004).

44 Kim, B. J. et al. In vitro and in vivo neuroprotective effects of cJun N-terminal kinase inhibitors on retinal ganglion cells. *Mol Neurodegener* 11, 30, doi:10.1186/s13024-016-0093-4 (2016).

45 Vaishnav, D., Jambal, P., Reusch, J. E. & Pugazhenthi, S. SP600125, an inhibitor of c-jun N-terminal kinase, activates CREB by a p38 MAPK-mediated pathway. *Biochem Biophys Res Commun* 307, 855-860, doi:10.1016/s0006-291x(03)01287-7 (2003).

46 Hong, J. et al. Lipopolysaccharide administration for a mouse model of cerebellar ataxia with neuroinflammation. *Sci Rep* 10, 13337, doi:10.1038/s41598-020-70390-7 (2020).

47 Zhao, J. et al. Neuroinflammation induced by lipopolysaccharide causes cognitive impairment in mice. *Sci Rep* 9, 5790, doi:10.1038/s41598-019-42286-8 (2019).

48 Sochocka, M., Diniz, B. S. & Leszek, J. Inflammatory Response in the CNS: Friend or Foe? v*Molecular Neurobiology* 54, 8071-8089, doi:10.1007/s12035-016-0297-1 (2017).

49 Hewett, S. J., Jackman, N. A. & Claycomb, R. J. Interleukin-1(3 in Central Nervous System Injury and Repair. *Eur J Neurodegener Dis* 1, 195-211 (2012).

50 Barnes, J. A. et al. Abnormalities in the Climbing Fiber-Purkinje Cell Circuitry Contribute to Neuronal Dysfunction in <em>ATXN1</em>[<em>82Q</em>] Mice. The Journal of Neuroscience 31, 12778, doi:10.1523/JNEUROSCI.2579-11.2011 (2011).

51 Ruegsegger, C. et al. Impaired mTORC1-Dependent Expression of Homer-3 Influences SCA1 Pathophysiology. *Neuron* 89, 129-146, doi:10.1016/j.neuron.2015.11.033 (2016).

52 Barnes, J. et al. Abnormalities in the Climbing Fiber-Purkinje Cell Circuitry Contribute to Neuronal Dysfunction in ATXN1[82Q] Mice. *The Journal of neuroscience: the official journal of the Society for Neuroscience* 31, 12778-12789, doi:10.1523/JNEUROSCI.2579-11.2011 (2011).

53 Perez-Catalan, N. A., Doe, C. Q. & Ackerman, S. D. The role of astrocyte-mediated plasticity in neural circuit development and function. *Neural Dev* 16, 1, doi:10.1186/s13064-020-00151-9 (2021).

54 Bernaus, A., Blanco, S. & Sevilla, A. Glia Crosstalk in Neuroinflammatory Diseases. *Frontiers in Cellular Neuroscience* 14, doi:10.3389/fncel.2020.00209 (2020).

55 Cerrato, V. Cerebellar Astrocytes: Much More Than Passive Bystanders In Ataxia Pathophysiology. *J Clin Med* 9, 757, doi:10.3390/jcm9030757 (2020).

56 Araujo, A. P. B., Carpi-Santos, R. & Gomes, F. C. A. The Role of Astrocytes in the Development of the Cerebellum. *Cerebellum* 18, 1017-1035, doi:10.1007/s12311-019-01046-0 (2019).

57 Andoh, T. et al. Protective Effect of IL-18 on Kainate- and IL-1β-Induced Cerebellar Ataxia in Mice. *The Journal of Immunology* 180, 2322, doi:10.4049/jimmunol.180.4.2322 (2008).

58 De Zeeuw, C. I. & Hoogland, T. M. Reappraisal of Bergmann glial cells as modulators of cerebellar circuit function. *Front Cell Neurosci* 9, 246, doi:10.3389/fncel.2015.00246 (2015).

59 Custer, S. K. et al. Bergmann glia expression of polyglutamine-expanded ataxin-7 produces neurodegeneration by impairing glutamate transport. *Nat Neurosci* 9, 1302-1311, doi:10.1038/nn1750 (2006).

60 Shiwaku, H., Yagishita, S., Eishi, Y. & Okazawa, H. Bergmann glia are reduced in spinocerebellar ataxia type 1. *NeuroReport* 24, 620-625 610.1097/WNR.1090b1013e32836347b32836347.

61 Cvetanovic, M. Decreased expression of glutamate transporter GLAST in Bergmann glia is associated with the loss of Purkinje neurons in the spinocerebellar ataxia type 1. *Cerebellum* 14, 8-11, doi:10.1007/s12311-014-0605-0 (2015).

62 Sasaki, T. et al. Application of an optogenetic byway for perturbing neuronal activity via glial photostimulation. *Proc Natl Acad Sci USA* 109, 20720-20725, doi:10.1073/pnas.1213458109 (2012).

63 Shuvaev, A. N. et al. Chronic optogenetic stimulation of Bergman glia leads to dysfunction of EAAT1 *Neurobiology of Disease* 154, 105340, doi:https://doi.org/10.1016/j.nbd.2021.105340 (2021).

64 Liddelow, S. A. et al. Neurotoxic reactive astrocytes are induced by activated microglia. *Nature* 541, 481-487, doi:10.1038/nature21029 (2017).

65 Rüb, U. et al. Clinical features, neurogenetics and neuropathology of the polyglutamine spinocerebellar ataxias type 1, 2, 3, 6 and 7. *Prog Neurobiol* 104, 38-66, doi:10.1016/j.pneurobio.2013.01.001 (2013).

66 Iltis, I. et al. (1)H MR spectroscopy in Friedreich's ataxia and ataxia with oculomotor apraxia type 2. *Brain Res* 1358, 200-210, doi:10.1016/j.brainres.2010.08.030 (2010).

67 Oppenheimer, D. R. Brain lesions in Friedreich's ataxia. *Can J Neurol Sci* 6, 173-176, doi:10.1017/s0317167100119596 (1979).

68 Reddy, C. E. et al. Multisite phosphorylation of c-Jun at threonine 91/93/95 triggers the onset of c-Jun pro-apoptotic activity in cerebellar granule neurons. *Cell Death Dis* 4, e852, doi:10.1038/cddis.2013.381 (2013).

The invention claimed is:

1. A method for treating a neurodegenerative disease or disorder in a subject in need thereof, the method comprising administering to the subject an effective amount of a c-Jun N-terminal kinase (JNK) inhibitor, wherein the neurodegenerative disease or disorder is a spinocerebellar ataxia type 1 (SCA1).

2. The method of claim 1, wherein the subject has Bergmann glia (BG)-specific JNK dependent c-Jun phosphorylation.

3. The method of claim 1, wherein the JNK inhibitor is a blood-brain-barrier permeating compound.

4. The method of claim 1, wherein the JNK inhibitor inhibits one or more isoforms of JNK.

5. The method of claim 1, wherein the JNK inhibitor is SP600125, AS601245, JNK-IN-1 or XG-102.

6. The method of claim 1 further comprising testing for the presence of a biomarker for the neurodegenerative disease or disorder in a biological sample from the subject and administering the effective amount of the JNK inhibitor if the biological sample tests positive for the biomarker, wherein the biomarker comprises a marker of c-Jun activation.

7. The method of claim 6, wherein the marker of c-Jun activation comprises phosphorylation of c-Jun.

* * * * *